(12) United States Patent
Riebel et al.

(10) Patent No.: US 6,346,503 B1
(45) Date of Patent: Feb. 12, 2002

(54) SUBSTITUTED 2-AMINO-4-ALKYLAMINO-1,3,5-TRIAZINES AS HERBICIDES

(75) Inventors: Hans-Jochem Riebel, Wuppertal; Stefan Lehr, Leverkusen; Uwe Stelzer, Burscheid, all of (DE); Yukiyoshi Watanbe, Oyama (JP); Markus Dollinger, Overland Park, KS (US)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/284,053

(22) Filed: Apr. 6, 1999

(30) Foreign Application Priority Data

Oct. 10, 1996 (DE) .......................... 196 41 691

(51) Int. Cl.$^7$ ................ A01N 43/68; A01N 43/70; C07D 251/18; C07D 251/58
(52) U.S. Cl. ............ 504/234; 504/232; 544/206; 544/208; 544/207; 544/209
(58) Field of Search ................. 504/234, 232; 544/206, 207, 208, 209

(56) References Cited

U.S. PATENT DOCUMENTS

| | | | | |
|---|---|---|---|---|
| 3,816,419 A | * | 6/1974 | Cross et al. ............... | 544/206 |
| 3,932,167 A | * | 1/1976 | Cross et al. ............... | 544/206 |
| 4,582,849 A | | 4/1986 | Marzolph et al. .......... | 514/425 |
| 5,011,996 A | | 4/1991 | Kiel et al. .................. | 564/321 |
| 5,290,754 A | | 3/1994 | Nishii et al. ................ | 504/232 |
| 5,403,815 A | | 4/1995 | Nishii et al. ................ | 504/230 |
| 5,728,876 A | | 3/1998 | Balkenhohl et al. ....... | 564/136 |
| 5,739,328 A | | 4/1998 | Schäfer et al. ............. | 544/194 |
| 5,744,621 A | | 4/1998 | Kim et al. ................... | 549/553 |
| 5,922,648 A | | 7/1999 | Lorenz et al. .............. | 504/232 |

FOREIGN PATENT DOCUMENTS

| | | |
|---|---|---|
| DE | 3221540 | 12/1983 |
| DE | 3426919 | 1/1986 |
| DE | 4000610 | 7/1991 |
| EP | 0 191 496 | 8/1986 |
| EP | 411153 | 2/1988 |
| EP | 273328 | 7/1988 |
| EP | 0 320 898 | 12/1988 |
| EP | 509544 | 10/1992 |
| WO | WO 97/08156 | 3/1997 |

OTHER PUBLICATIONS

J. Med. Chem., Jul. 1967, vol. 10, pp. 717–724, Schultz et al, Maleamic Acids that Affect Plasma Cholesterol and Penicillin Excretion.

J. Am Chem. Soc., Oct.–Dec. 1975, pp. 6900–6901, Dunrante et al, The Oxidative Deamination of Amines to Ketones via Oxaziridines.

Tetrahedron Letters, vol. 35, No. 22, pp. 3745–3746, Son et al, An Efficient and Enantioselective Synthesis of A Chiral Primary Amine.

Tetrahedron: Asymmetry, vol. 5, pp. 817–820 (month unavailable) 1994, Calmes et al Asymmetric Supported Reaction: Synthesis of Chiral Amines.

Tetrahedron Letters, vol. 29, No. 2, pp. 223–224, (month unavailable) 1988, Sakito et al Asymmetric Reduction of Oxime Ethers. Distinction of Anti and Syn Isomers Leading to Enantiomeric Amines.

Tetrahedron Letters, vol. 36, No. 22 pp. 3917–3920, (month unavailable) 1995, Willems et al Asymmetric Imine Isomerisation in the Enantioselective Synthesis of Chiral Amines from Prochiral Ketons.

* cited by examiner

*Primary Examiner*—John M. Ford
(74) *Attorney, Agent, or Firm*—Joseph C. Gil; James R. Franks; Jackie Ann Zurcher

(57) ABSTRACT

The invention relates to novel substituted 2-amino-4-alkylamino-1,3,5-triazines of the formula (I)

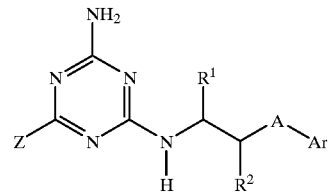

(I)

in which $R^1$ represents in each case optionally substituted alkyl having 2 to 6 carbon atoms or cycloalkyl having 3 to 6 carbon atoms, $R^2$ represents hydrogen or represents alkyl having 1 to 4 carbon atoms, A represents oxygen or methylene, Ar represents in each case optionally substituted phenyl, naphthyl or heterocyclyl, and Z represents hydrogen, represents halogen or represents in each case optionally substituted alkyl, alkoxy, alkylcarboxyl, alkoxycarbonyl, alkylthio, alkylsulphinyl, alkylsulphonyl, alkenyl or alkinyl, to processes and to novel intermediates for their preparation and to their use as herbicides.

4 Claims, No Drawings

SUBSTITUTED 2-AMINO-4-ALKYLAMINO-1,3,5-TRIAZINES AS HERBICIDES

TECHNICAL FIELD OF THE INVENTION

The invention relates to novel substituted 2-amino-4-alkylarnino-1,3,5-triazines, to processes and to novel intermediates for their preparation and to their use as herbicides.

BACKGROUND OF THE INVENTION

A number of substituted 2,4-diamino-triazines is already known from the (patent) literature (cf. U.S. Pat. No. 3,816,419, U.S. Pat. No. 3,932,167, EP 191496, EP 273328, EP 411153/WO 90/09378, WO 97/00254, WO 97/08156). However, these compounds have hitherto not attained any particular importance.

DETAILED DESCRIPTION OF THE INVENTION

This invention, accordingly, provides the novel substituted 2-amino-4-alkylamino-1,3,5-triazines of the general formula (I)

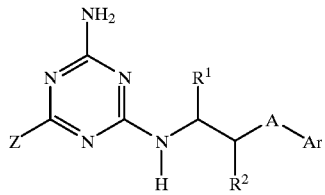

(I)

in which
  $R^1$ represents in each case optionally substituted alkyl having 2 to 6 carbon atoms or cycloalkyl having 3 to 6 carbon atoms,
  $R^2$ represents hydrogen or represents alkyl having 1 to 4 carbon atoms,
  A represents oxygen or methylene
  Ar represents in each case optionally substituted phenyl, naphthyl or heterocyclyl, and
  Z represents hydrogen, represents halogen or represents in each case optionally substituted alkyl, alkoxy, alkylcarbonyl, alkoxycarbonyl, alkylthio, alkylsulphinyl, alkylsulphonyl, alkenyl or alkinyl.

The novel 2-amino-4-alkylamino-1,3,5-triazines of the general formula (I) are obtained when
  (a) substituted biguanides of the general formula (II),

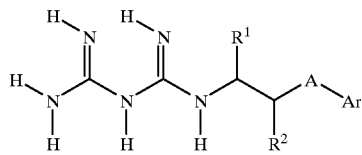

(II)

in which
  $R^1$, $R^2$, A and Ar are each as defined above —and/or acid adducts of compounds of the general formula (II)—are reacted with alkoxycarbonyl compounds of the general formula (III)

Z—CO—OR'  (III)

in which
  Z is as defined above and
  R' represents alkyl,
if appropriate in the presence of a reaction auxiliary and if appropriate in the presence of a diluent,
or when
  (b) substituted triazines of the general formula (IV)

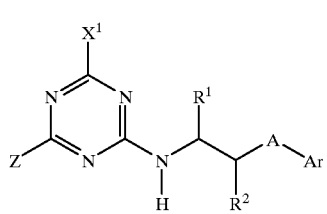

(IV)

in which
  $R^1$, $R^2$, A, Ar and Z are each as defined above and
  $X^1$ represents halogen or alkoxy
    are reacted with ammonia, if appropriate in the presence of a reaction auxiliary and if appropriate in the presence of a diluent,
or when
  (c) substituted triazines of the general formula (V),

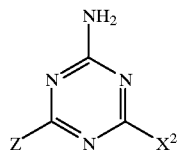

(V)

in which
  Z is as defined above and
  $X^2$ represents halogen or alkoxy
    are reacted with substituted alkylamines of the general formula (VI),

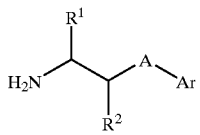

(VI)

in which
  $R^1$, $R^2$, A and Ar are each as defined above,
if appropriate in the presence of a reaction auxiliary and if appropriate in the presence of a diluent,
and, if appropriate, further conversions within the scope of the above definition of substituents are carried out by customary methods on the compounds of the general formula (I) obtained by the processes described under (a), (b) or (c).

The novel substituted 2-amino-4-alkylamino-1,3,5-triazines of the general formula (I) have strong and selective herbicidal activity.

The compounds of the general formula (I) according to the invention contain at least one asymmetrically substituted carbon atom and can therefore be present in different enantiomeric (R- and S-configured forms) or diastereomeric forms. The invention relates both to the different possible individual enantiomeric or stereoisomeric forms of the compounds of the general formula (I), and to the mixtures of these isomeric compounds.

In the definitions, the hydrocarbon chains, such as alkyl—also in combination with heteroatoms, such as in alkoxy or alkylthio—are in each case straight-chain or branched.

Halogen generally represents fluorine, chlorine, bromine or iodine, preferably represents fluorine, chlorine or bromine, and in particular represents fluorine or chlorine.

The invention preferably provides compounds of the formula (I) in which $R^1$ represents optionally hydroxyl-, cyano-, halogen- or $C_1$–$C_4$-alkoxy-substituted alkyl having 2 to 4 carbon atoms or represents optionally cyano-, halogen- or $C_1$–$C_4$-alkyl-substituted cycloalkyl having 3 to 6 carbon atoms, $R^2$ represents hydrogen, methyl or ethyl, A represents oxygen or methylene, Ar represents in each case optionally substituted phenyl, naphthyl or heterocyclyl, where the possible heterocyclyl groupings are preferably selected from the group below:

furyl, benzofuryl, dihydrobenzofuryl, tetrahydrofuryl, thienyl, benzothienyl, thiazolyl, benzothiazolyl, oxazolyl, benzoxazolyl, thiadiazolyl, oxadiazolyl, pyrazolyl, pyrrolyl, quinolinyl, isoquinolinyl, pyridinyl and pyrimidinyl, and where the possible substituents are in each case preferably selected from the group below:

hydroxyl, cyano, nitro, halogen, in each case optionally hydroxyl-, cyano- or halogen-substituted alkyl or alkoxy having in each case 1 to 6 carbon atoms, in each case optionally halogen-substituted alkylcarbonyl, alkoxycarbonyl, alkylthio, alkylsulphinyl or alkylsulphonyl having in each case 1 to 6 carbon atoms in the alkyl groups, in each case optionally hydroxyl-, cyano-, nitro-, halogen-, $C_1$–$C_4$-alkyl, $C_1$–$C_4$-halogenoalkyl, $C_1$–$C_4$-alkoxy- or $C_1$–$C_4$-halogenoalkoxy-substituted phenyl or phenoxy, and also in each case optionally halogen-substituted methylenedioxy or ethylenedioxy, and Z represents hydrogen, represents halogen, represents in each case optionally hydroxyl-, cyano-, nitro-, halogen-, $C_1$–$C_4$-alkoxy-, $C_1$–$C_4$-alkyl-carbonyl-, $C_1$–$C_4$-alkoxy-carbonyl-, $C_1$–$C_4$-alkylthio-, $C_1$–$C_4$-alkylsulphinyl- or $C_1$–$C_4$-alkylsulphonyl-substituted alkyl, alkoxy, alkylcarbonyl, alkoxycarbonyl, alkylthio, alkylsulphinyl or alkylsulphonyl having in each case 1 to 6 carbon atoms in the alkyl groups, or represents in each case optionally halogen-substituted alkenyl or alkinyl having in each case 2 to 6 carbon atoms.

From among the compounds of the formula (I) defined above as preferred ("preferably"), particular emphasis is given to the following groups:

(A) the compounds of the formula (I) in which A, $R^1$, $R^2$ and Z are each as defined above and Ar represents in each case optionally substituted phenyl or naphthyl, the possible substituents being as defined above;

(B) the compounds of the formula (I) in which A, $R^1$, $R^2$ and Z are each as defined above and Ar represents in each case optionally substituted heterocyclyl, the possible heterocyclyl groupings and the possible substituents being as defined above.

The invention in particular relates to compounds of the formula (I) in which $R^1$ represents in each case optionally hydroxyl-, cyano-, fluorine-, chlorine-, methoxy- or ethoxy-substituted ethyl, n- or i-propyl, n-, i-, s- or t-butyl or represents in each case optionally cyano-, fluorine-, chlorine-, methyl- or ethyl-substituted cyclopropyl, cyclobutyl, cyclopentyl or cyclohexyl, $R^2$ represents hydrogen or methyl, A represents oxygen or methylene, Ar represents in each case optionally substituted phenyl, naphthyl or heterocyclyl, where the possible heterocyclyl groups are preferably selected from the group below:

furyl, benzofuryl, dihydrobenzofuryl, tetrahydrofuryl, thienyl, benzothienyl, thiazolyl, benzothiazolyl, oxazolyl, benzoxazolyl, thiadiazolyl, oxadiazolyl, pyrazolyl, pyrrolyl, quinolinyl, isoquinolinyl, pyridinyl and pyrimidinyl, and where the possible substituents are in each case preferably selected from the group below:

hydroxyl, cyano, nitro, fluorine, chlorine, bromine, in each case optionally hydroxyl- cyano-, fluorine- or chlorine-substituted methyl, ethyl, n- or i-propyl, n-, i-, s- or t-butyl, methoxy, ethoxy, n- or i-propoxy, n-, i-, s- or t-butoxy, in each case optionally fluorine- or chlorine-substituted acetyl, propionyl, n- or i-butyroyl, methoxycarbonyl, ethoxycarbonyl, n- or i-propoxycarbonyl, methylthio, ethylthio, n- or i-propylthio, methylsulphinyl, ethylsulphinyl, n- or i-propylsulphinyl, methylsulphonyl, ethylsulphonyl, n- or i-propylsulphonyl, in each case optionally hydroxyl-, cyano-, nitro-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substituted phenyl or phenoxy, and also in each case optionally fluorine- or chlorine-substituted methylenedioxy or ethylenedioxy, and Z represents hydrogen, fluorine, chlorine, bromine, represents in each case optionally hydroxyl-, cyano-. nitro-. fluorine-, chlorine-, methoxy-, ethoxy-, n- or i-propoxy-, n-, i-, s- or t-butoxy-, methylthio-ethylthio-, n- or i-propylthio-, methylsulphinyl-, ethylsulphinyl-, n- or i-propylsulphinyl-, methylsulphonyl-, ethylsulphonyl-, n- or i-propylsulphonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl, or represents in each case optionally fluorine-, chlorine- or bromine-substituted ethenyl, propenyl, butenyl, ethinyl, propinyl or butinyl.

From among the compounds of the formula (I) defined above as being particularly preferred, particular emphasis is given to the following groups:

(AA) the compounds of the formula (1) in which A, $R^1$, $R^2$ and Z are each as defined above and Ar represents in each case optionally substituted phenyl or naphthyl, the possible substituents being as defined above, with the proviso that the substituents of the carbon atom to which $R^1$ is attached are arranged in the R configuration;

(BB) the compounds of the formula (I) in which A, $R^1$, $R^2$ and Z are each as defined above and Ar represents in each case optionally substituted phenyl or naphthyl, the possible substituents being as defined above, with the proviso that the substituents of the carbon atom to which $R^1$ is attached are arranged in the S configuration;

(CC) the compounds of the formula (I) in which A, $R^1$, $R^2$ and Z are each as defined above and Ar represents in each case optionally substituted furyl, thienyl, pyridinyl or pyrimidinyl, the possible substituents being as defined above, with the proviso that these compounds are present as racemic mixtures;

(DD) the compounds of the formula (I) in which A, $R^1$, $R^2$ and Z are each as defined above and Ar represents in each case optionally substituted furyl, thienyl, pyridinyl or pyrimidinyl, the possible substituents being as defined above, with the proviso that the substituents of the carbon atom to which $R^1$ is attached are arranged in the R configuration;

(EE) the compounds of the formula (I), in which A, $R^1$, $R^2$ and Z are each as defined above and Ar represents in each case optionally substituted furyl, thienyl, pyridinyl or pyrimidinyl, the possible substituents being as defined above, with the proviso that the substituents of the carbon atom to which $R^1$ is attached are arranged in the S configuration;

The abovementioned general or preferred radical definitions apply both to the end products of the formula (I) and also, correspondingly, to the starting materials or intermediates required in each case for the preparation. These radical definitions can be combined with each other at will, i.e. including combinations between the abovementioned preferred ranges.

Examples of the compounds of the formula (I) according to the invention are listed in the groups below. The general formulae here represent in each case the R enantiomers, the S enantiomers and the racemates.

Group 1

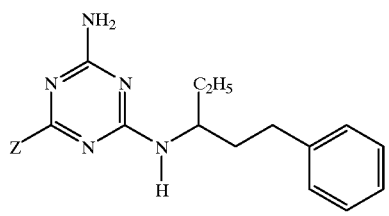

(I-1)

Here, Z has, for example, the meanings given below:

Hydrogen, methyl, ethyl, n- or i-propyl, n-, i-, s- or t-butyl, fluoromethyl, difluoromethyl, trifluoromethyl, chloromethyl, dichloromethyl, chlorofluoromethyl, chlorobromomethyl, chlorodifluoromethyl, fluorodichloromethyl, bromodifluoromethyl, trichloromethyl, 1-fluoro-ethyl, 2-fluoro-ethyl, 1-chloro-ethyl, 2-chloroethyl, 1-chloro-1-fluoro-ethyl, 1-fluoro-propyl, 2-fluoro-propyl, 3-fluoro-propyl, 1-fluoro-1-methyl-ethyl, 2-fluoro-1-methyl-ethyl, 1-chloro-1-methyl-ethyl, 1-fluoro-1-methyl-propyl, 1-chloro-1-ethyl-propyl, 1-fluoro-1-ethyl-propyl, 1-chloro-1-ethylpropyl, 1-fluoro-2-methyl-propyl, 1-chloro-2-methyl-propyl, 1-chloro-propyl, 2-chloro-propyl, 3-chloro-propyl, 1-chloro-1-methyl-ethyl, 2-chloro-1-methyl-ethyl, 1,1-difluoro-ethyl, 1,2-difluoro-ethyl, 1,1-dichloro-ethyl, 2,2,2-trifluoro-ethyl, 1,2,2,2-tetrafluoro-ethyl, perfluoroethyl, 1,1-difluoro-propyl, 1,1-dichloro-propyl, perfluoropropyl, 1-fluoro-butyl, 1-chloro-butyl, perfluoropentyl, perfluorohexyl, 1-hydroxyl-ethyl, acetyl, 1,1-bis-acetyl-methyl, 1-acetyl-1-methoxycarbonyl-methyl, 1-acetyl-1-ethoxycarbonyl-methyl, methoxymethyl, 1,1-dimethoxy-methyl, 1-methoxyethyl, 2-methoxy-ethyl, 1,1-dimethoxy-ethyl, ethoxymethyl, 1-ethoxyethyl, 2-ethoxy-ethyl, 2-methoxy-1-methyl-ethyl, 2-methoxy-1-ethyl-ethyl, 2-ethoxy-1-methyl-ethyl, 2-ethoxy-1-ethyl-ethyl, methylthiomethyl, ethylthiomethyl, 1-methylthio-ethyl, 2-methylthioethyl, 1-ethylthio-ethyl, 2-ethylthioethyl, methylsulphinylmethyl, ethylsulphinylmethyl, methylsulphonylmethyl, ethylsulphonylmethyl, methoxy, ethoxy, n- or i- propoxy, methylthio, ethylthio, n- or i-propylthio, methylsulphinyl, ethylsulphinyl, methylsulphonyl, ethylsulphonyl, fluoromethoxy, difluoromethoxy, trifluoromethoxy, fluoroethoxy, difluoroethoxy, trifluoroethoxy, difluoromethylthio, trifluoromethylthio, vinyl, 1-chloro-vinyl, 2-chloro-vinyl, 1-fluoro-vinyl, 2-fluoro-vinyl, 1-bromo-vinyl, 2-bromo-vinyl, 1,2-dichloro-vinyl, 1,2-dibromo-vinyl, 1,2-difluoro-vinyl, 2,2-dichloro-vinyl, 2,2-difluoro-vinyl, 2,2-dibromo-vinyl, 1-chloro-2-fluoro-vinyl, 2-bromo-2-chloro-vinyl, trichlorovinyl, allyl, 2-chloro-allyl, 3-chloro-allyl, 3,3-dichloro-allyl, 1-propenyl, isopropenyl, 1-chloro-2-propenyl, 1-fluoro-2-propenyl, 1-bromo-2-propenyl, 1,2-dichloro-1-propenyl, 1,2-dibromo-1-propenyl, 1,2-difluoro-1-propenyl, 1,1-dichloro-2-propenyl, 1,1-dibromo-2-propenyl, 1,1-difluoro-2-propenyl, 1,1,3,3,3-pentafluoro-2-propenyl, 2-buten-1-yl, 2-buten-2-yl, 3-chloro-2-butenyl, 3-bromo-2-butenyl, 3,3,3-trifluoro-2-butenyl, ethinyl, 2-chloro-ethinyl, 2-bromo-ethinyl, 1-propinyl, 2-propinyl, 3,3,3-trifluoro-1-propinyl.

Group 2

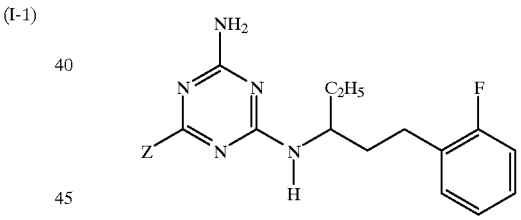

(I-2)

Here, Z has, for example, the meanings given above in group 1.

Group 3

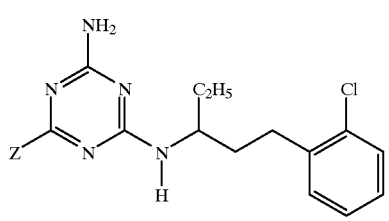

(I-3)

Here, Z has, for example, the meanings given above in group 1.

Group 4

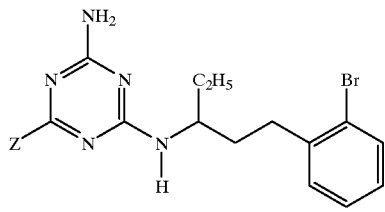

(I-4)

Here, Z has, for example, the meanings given above in group 1.

Group 5

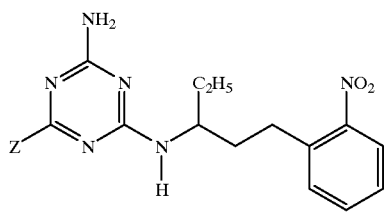

(I-5)

Here, Z has, for example, the meanings given above in group 1.

Group 6

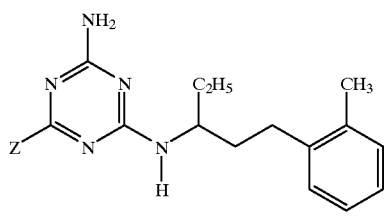

(I-6)

Here, Z has, for example, the meanings given above in group 1.

Group 7

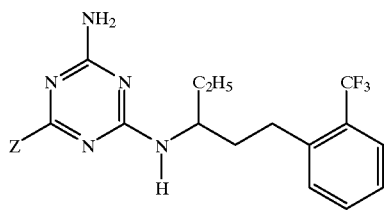

(I-7)

Here, Z has, for example, the meanings given above in group 1.

Group 8

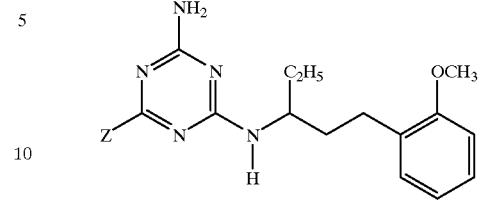

(I-8)

Here, Z has, for example, the meanings given above in group 1.

Group 9

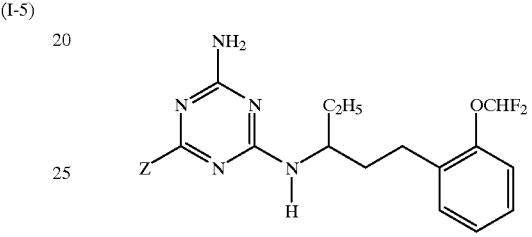

(I-9)

Here, Z has, for example, the meanings given above in group 1.

Group 10

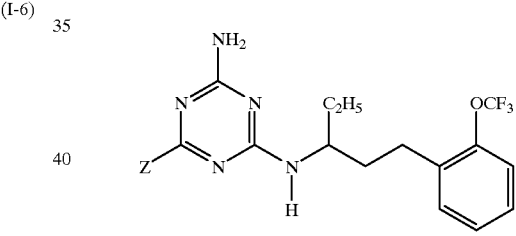

(I-10)

Here, Z has, for example, the meanings given above in group 1.

Group 11

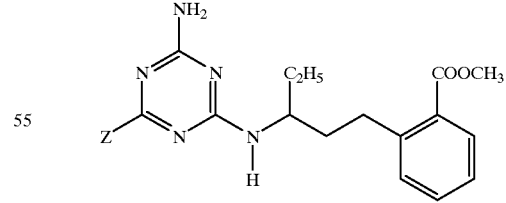

(I-11)

Here, Z has, for example, the meanings given above in group 1.

Group 12

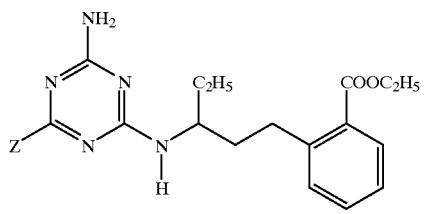
(I-12)

Here, Z has, for example, the meanings given above in group 1.

Group 13

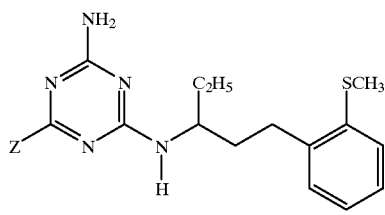
(I-13)

Here, Z has, for example, the meanings given above in group 1.

Group 14

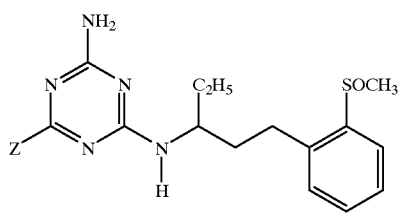
(I-14)

Here, Z has, for example, the meanings given above in group 1.

Group 15

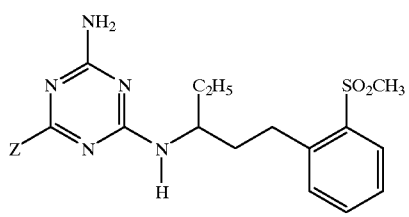
(I-15)

Here, Z has, for example, the meanings given above in group 1.

Group 16

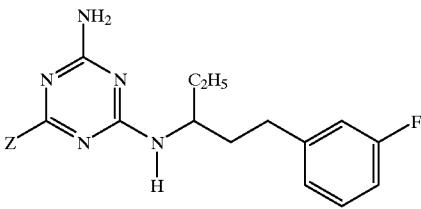
(I-16)

Here, Z has, for example, the meanings given above in group 1.

Group 17

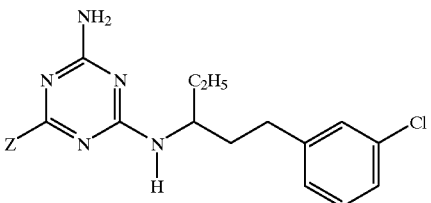
(I-17)

Here, Z has, for example, the meanings given above in group 1.

Group 18

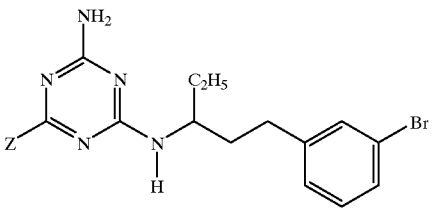
(I-18)

Here, Z has, for example, the meanings given above in group 1.

Group 19

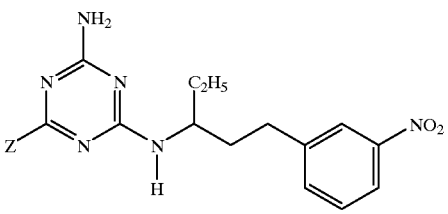
(I-19)

Here, Z has, for example, the meanings given above in group 1.

Group 20

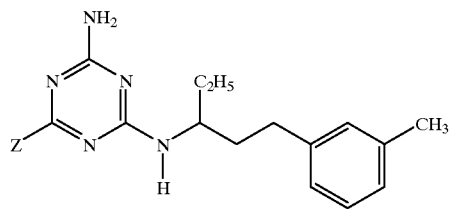

(I-20)

Here, Z has, for example, the meanings given above in group 1.

Group 21

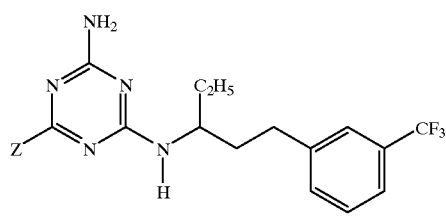

(I-21)

Here, Z has, for example, the meanings given above in group 1.

Group 22

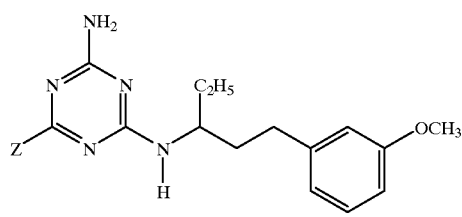

(I-22)

Here, Z has, for example, the meanings given above in group 1.

Group 23

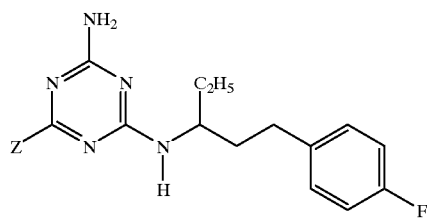

(I-23)

Here, Z has, for example, the meanings given above in group 1.

Group 24

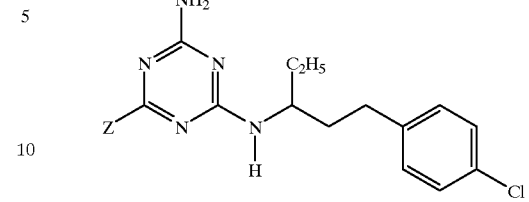

(I-24)

Here, Z has, for example, the meanings given above in group 1.

Group 25

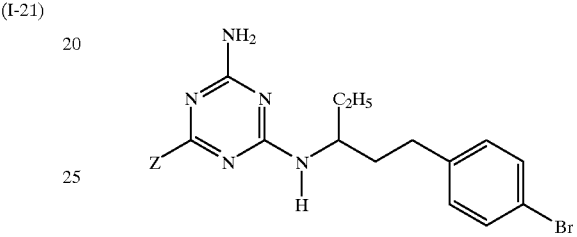

(I-25)

Here, Z has, for example, the meanings given above in group 1.

Group 26

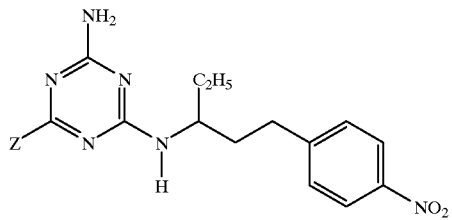

(I-26)

Here, Z has, for example, the meanings given above in group 1.

Group 27

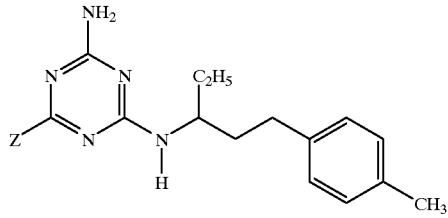

(I-27)

Here, Z has, for example, the meanings given above in group 1.

Group 28

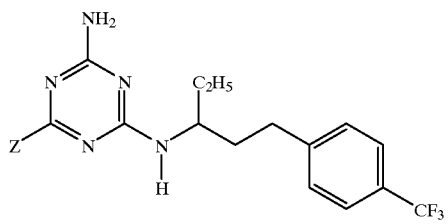
(I-28)

Here, Z has, for example, the meanings given above in group 1.

Group 29

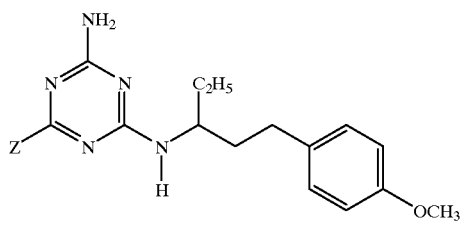
(I-29)

Here, Z has, for example, the meanings given above in group 1.

Group 30

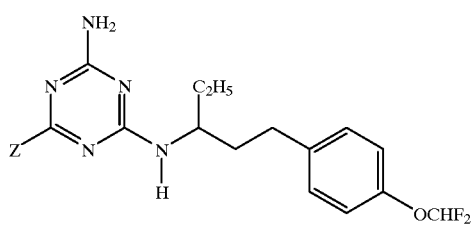
(I-30)

Here, Z has, for example, the meanings given above in group 1.

Group 31

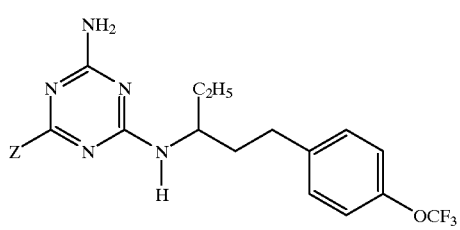
(I-31)

Here, Z has, for example, the meanings given above in group 1.

Group 32

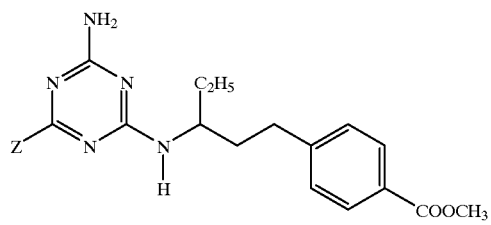
(I-32)

Here, Z has, for example, the meanings given above in group 1.

Group 33

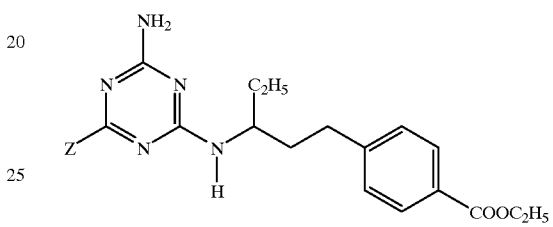
(I-33)

Here, Z has, for example, the meanings given above in group 1.

Group 34

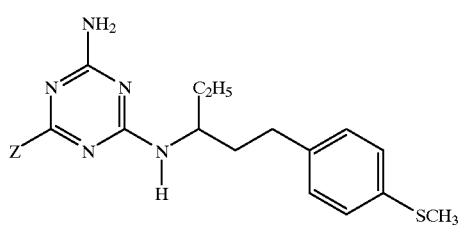
(I-34)

Here, Z has, for example, the meanings given above in group 1.

Group 35

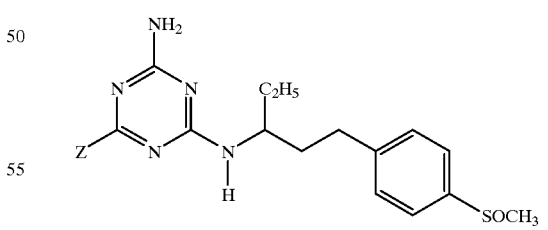
(I-35)

Here, Z has, for example, the meanings given above in group 1.

Group 36

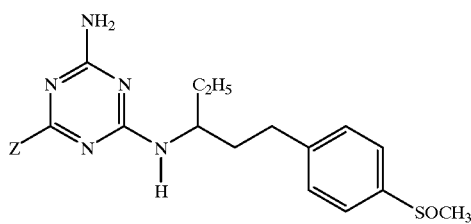
(I-36)

Here, Z has, for example, the meanings given above in group 1.

Group 37

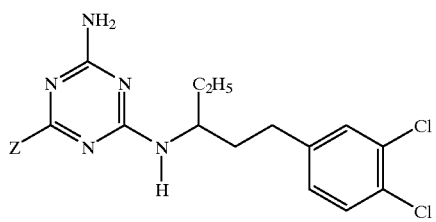
(I-37)

Here, Z has, for example, the meanings given above in group 1.

Group 38

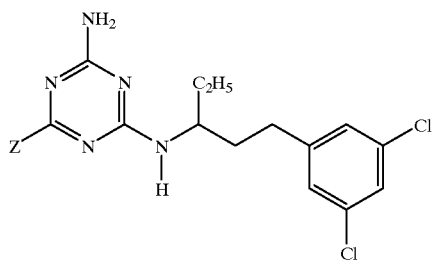
(I-38)

Here, Z has, for example, the meanings given above in group 1.

Group 39

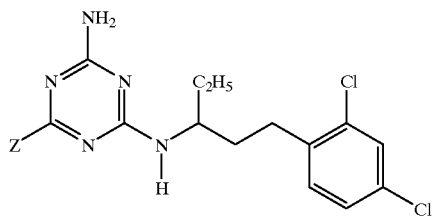
(I-39)

Here, Z has, for example, the meanings given above in group 1.

Group 40

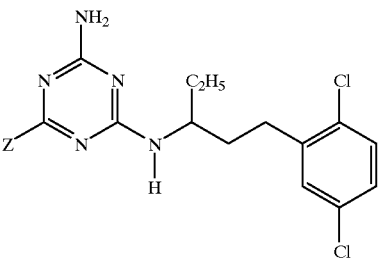
(I-40)

Here, Z has, for example, the meanings given above in group 1.

Group 41

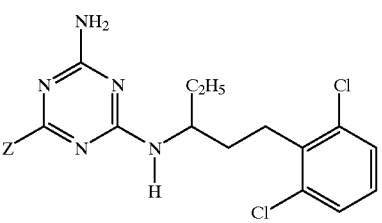
(I-41)

Here, Z has, for example, the meanings given above in group 1.

Group 42

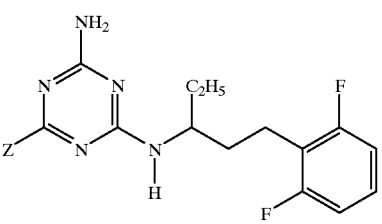
(I-42)

Here, Z has, for example, the meanings given above in group 1.

Group 43

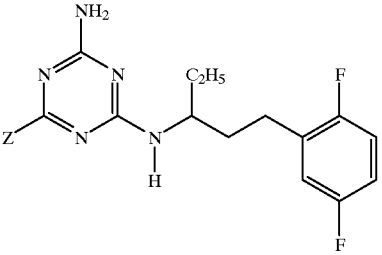
(I-43)

Here, Z has, for example, the meanings given above in group 1.

Group 44

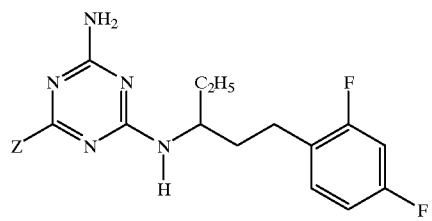
(I-44)

Here, Z has, for example, the meanings given above in group 1.

Group 45

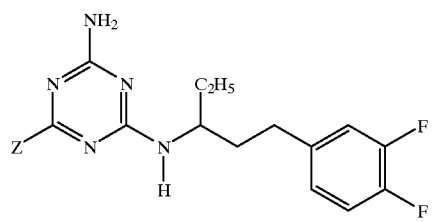
(I-45)

Here, Z has, for example, the meanings given above in group 1.

Group 46

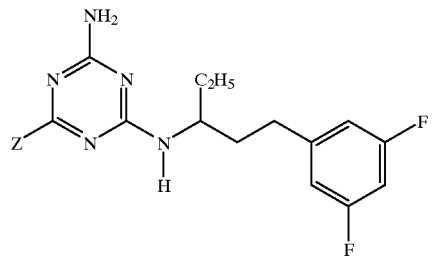
(I-46)

Here, Z has, for example, the meanings given above in group 1.

Group 47

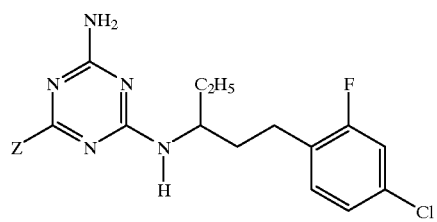
(I-47)

Here, Z has, for example, the meanings given above in group 1.

Group 48

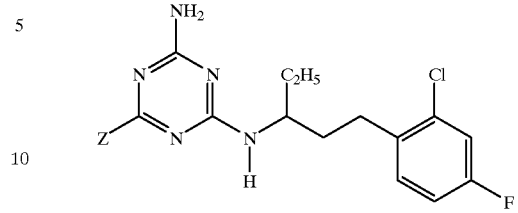
(I-48)

Here, Z has, for example, the meanings given above in group 1.

Group 49

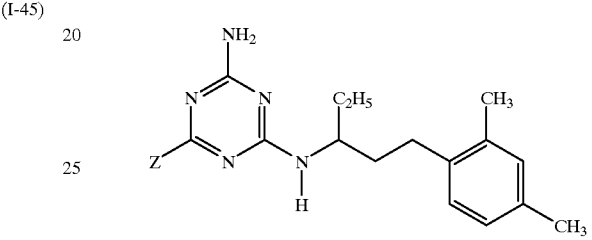
(I-49)

Here, Z has, for example, the meanings given above in group 1.

Group 50

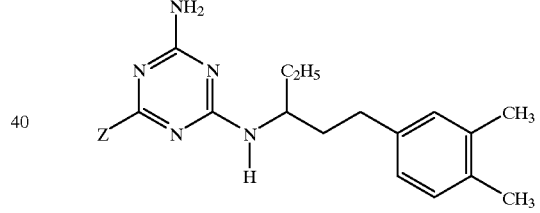
(I-50)

Here, Z has, for example, the meanings given above in group 1.

Group 51

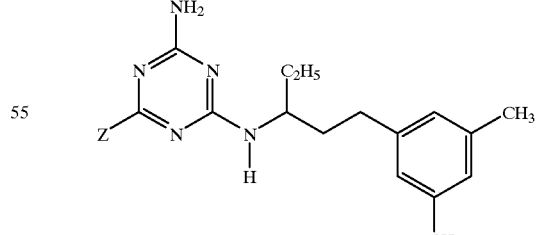
(I-51)

Here, Z has, for example, the meanings given above in group 1.

Group 52

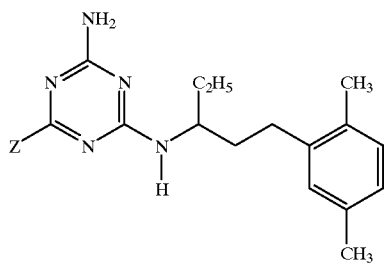
(I-52)

Here, Z has, for example, the meanings given above in group 1.

Group 53

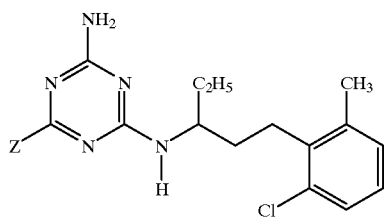
(I-53)

Here, Z has, for example, the meanings given above in group 1.

Group 54

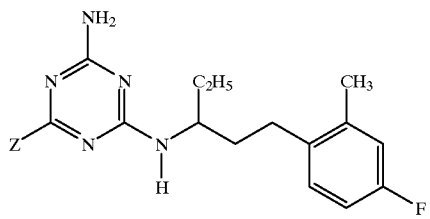
(I-54)

Here, Z has, for example, the meanings given above in group 1.

Group 55

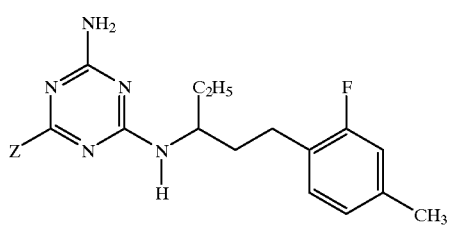
(I-55)

Here, Z has, for example, the meanings given above in group 1.

Group 56

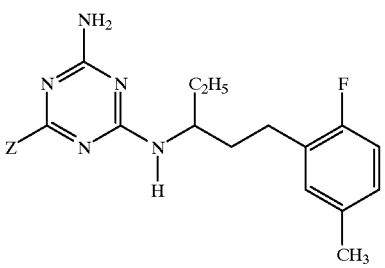
(I-56)

Here, Z has, for example, the meanings given above in group 1.

Group 57

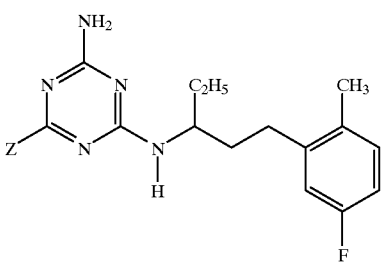
(I-57)

Here, Z has, for example, the meanings given above in group 1.

Group 58

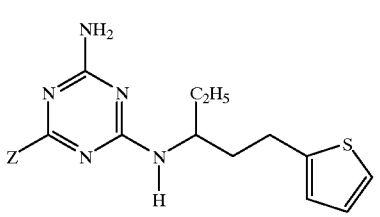
(I-58)

Here, Z has, for example, the meanings given above in group 1.

Group 59

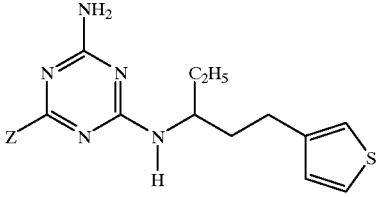
(I-59)

Here, Z has, for example, the meanings given above in group 1.

Group 60

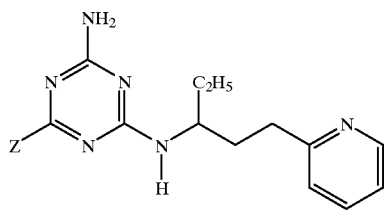
(I-60)

Here, Z has, for example, the meanings given above in group 1.

Group 61

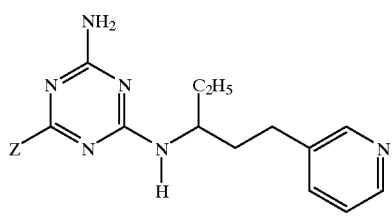
(I-61)

Here, Z has, for example, the meanings given above in group 1.

Group 62

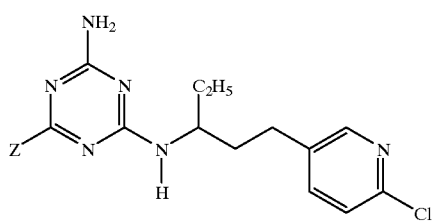
(I-62)

Here, Z has, for example, the meanings given above in group 1.

Group 63

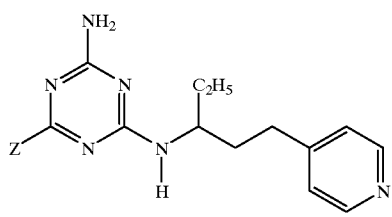
(I-63)

Here, Z has, for example, the meanings given above in group 1.

Group 64

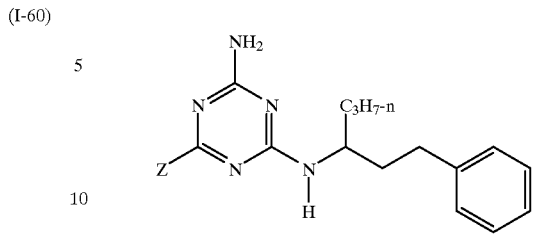
(I-64)

Here, Z has, for example, the meanings given above in group 1.

Group 65

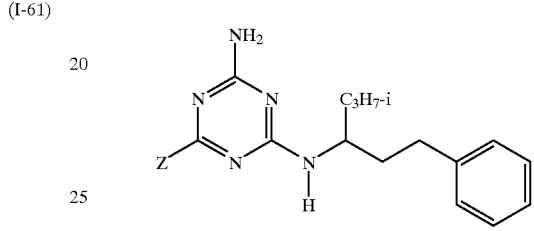
(I-65)

Here, Z has, for example, the meanings given above in group 1.

Group 66

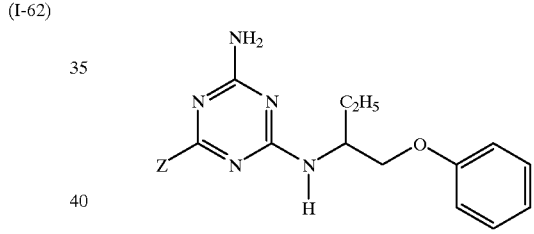
(I-66)

Here, Z has, for example, the meanings given above in group 1.

Group 67

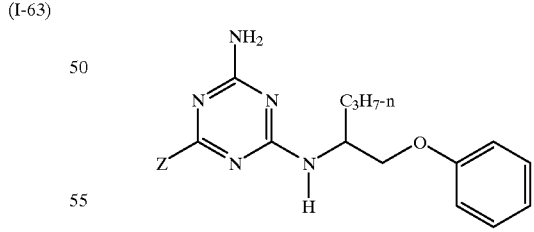
(I-67)

Here, Z has, for example, the meanings given above in group 1.

Group 68

(I-68)

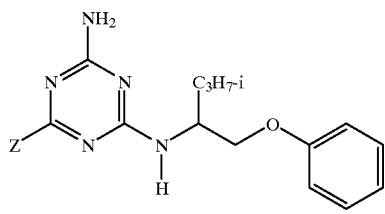

Here, Z has, for example, the meanings given above in group 1.

Group 69

(I-69)

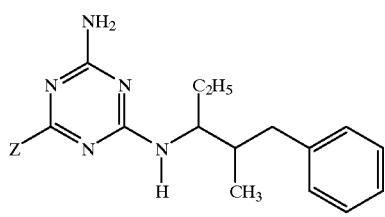

Here, Z has, for example, the meanings given above in group 1.

Group 70

(I-70)

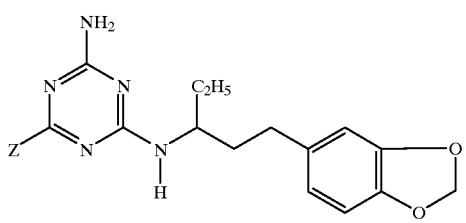

Here, Z has, for example, the meanings given above in group 1.

Group 71

(I-71)

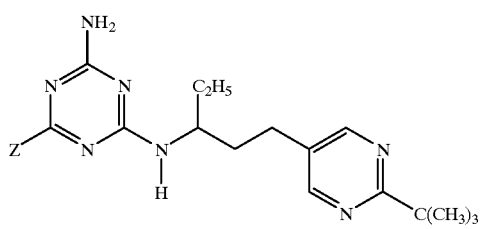

Here, Z has, for example, the meanings given above in group 1.

Group 72

(I-72)

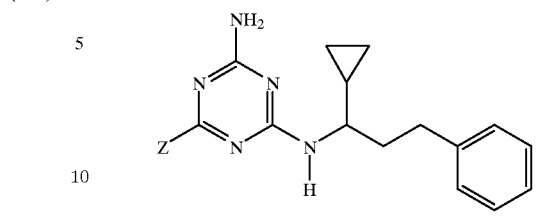

Here, Z has, for example, the meanings given above in group 1.

Group 73

(I-73)

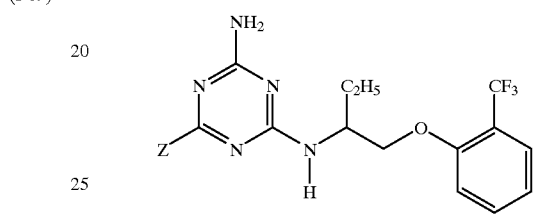

Here, Z has, for example, the meanings given above in group 1.

Group 74

(I-74)

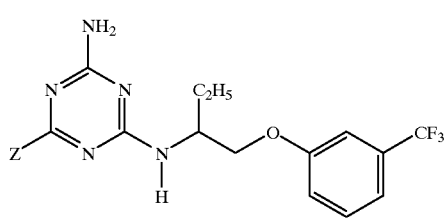

Here, Z has, for example, the meanings given above in group 1.

Group 75

(I-75)

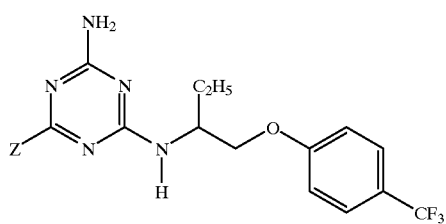

Here, Z has, for example, the meanings given above in group 1.

Group 76

(I-76)

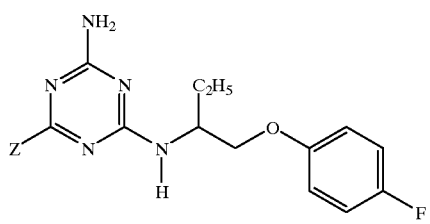

Here, Z has, for example, the meanings given above in group 1.

Group 77

(I-77)

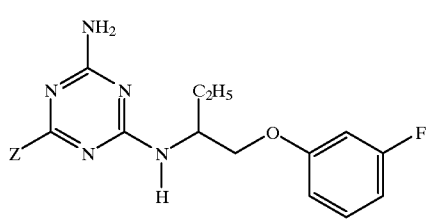

Here, Z has, for example, the meanings given above in group 1.

Group 78

(I-78)

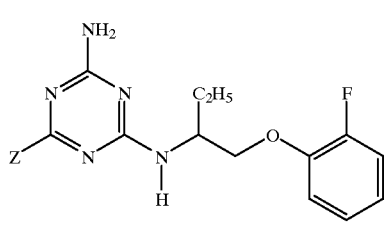

Here, Z has, for example, the meanings given above in group 1.

Group 79

(I-79)

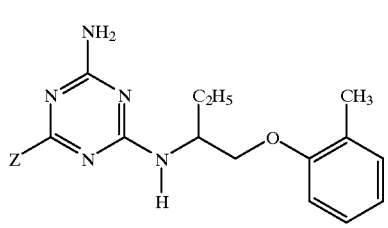

Here, Z has, for example, the meanings given above in group 1.

Group 80

(I-80)

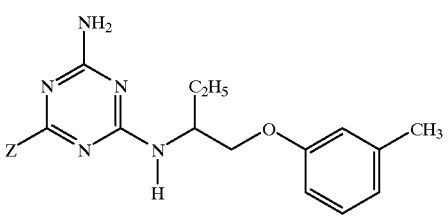

Here, Z has, for example, the meanings given above in group 1.

Group 81

(I-81)

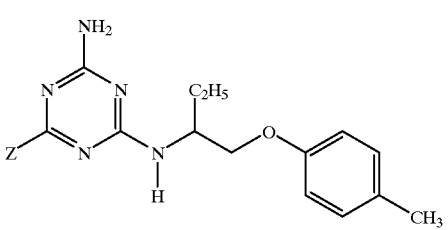

Here, Z has, for example, the meanings given above in group 1.

Group 82

(I-82)

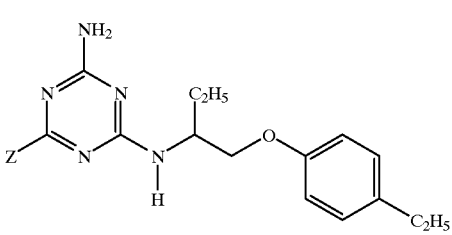

Here, Z has, for example, the meanings given above in group 1.

Group 83

(I-83)

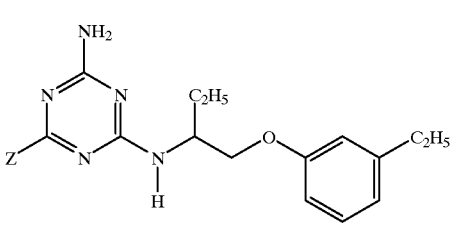

Here, Z has, for example, the meanings given above in group 1.

Group 84

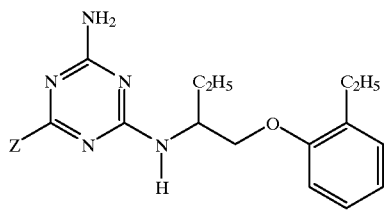
(I-84)

Here, Z has, for example, the meanings given above in group 1.

Group 85

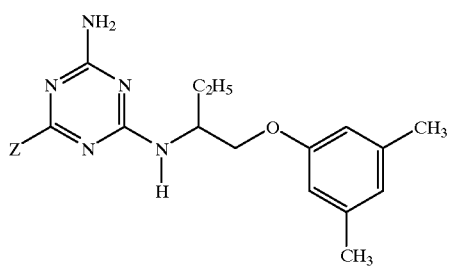
(I-85)

Here, Z has, for example, the meanings given above in group 1.

Group 86

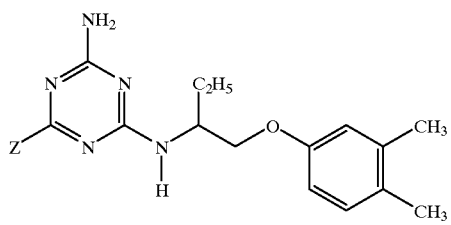
(I-86)

Here, Z has, for example, the meanings given above in group 1.

Group 87

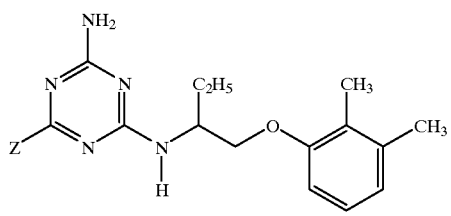
(I-87)

Here, Z has, for example, the meanings given above in group 1.

Group 88

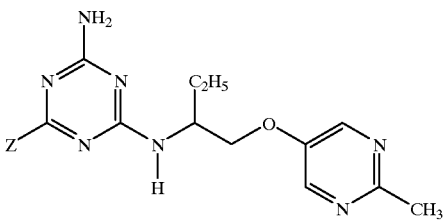
(I-88)

Here, Z has, for example, the meanings given above in group 1.

Group 89

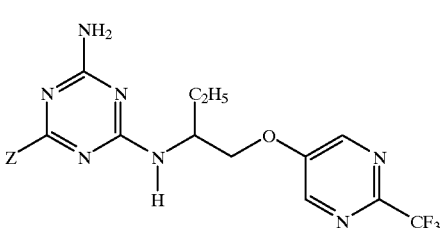
(I-89)

Here, Z has, for example, the meanings given above in group 1.

Group 90

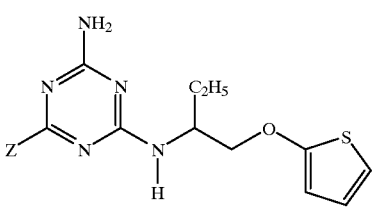
(I-90)

Here, Z has, for example, the meanings given above in group 1.

Group 91

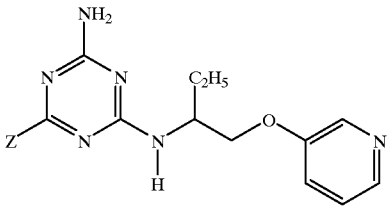
(I-91)

Here, Z has, for example, the meanings given above in group 1.

Group 92

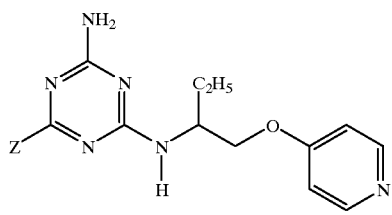
(I-92)

Here, Z has, for example, the meanings given above in group 1.

Group 93

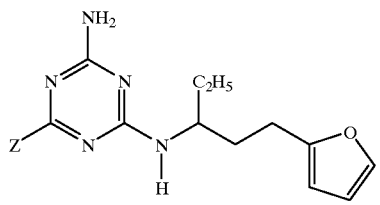
(I-93)

Here, Z has, for example, the meanings given above in group 1.

Group 94

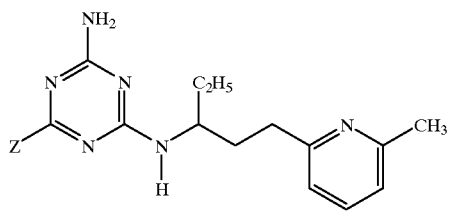
(I-94)

Here, Z has, for example, the meanings given above in group 1.

Group 95

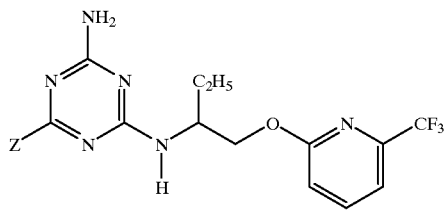
(I-95)

Here, Z has, for example, the meanings given above in group 1.

Group 96

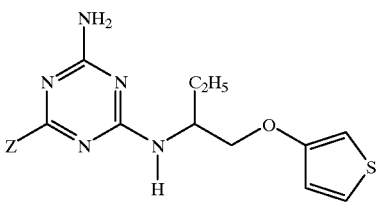
(I-96)

Here, Z has, for example, the meanings given above in group 1.

Group 97

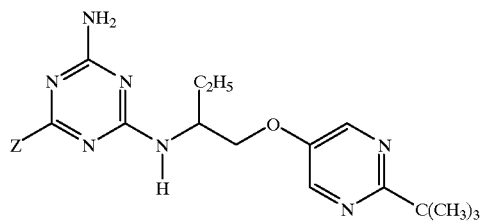
(I-97)

Here, Z has, for example, the meanings given above in group 1.

Group 98

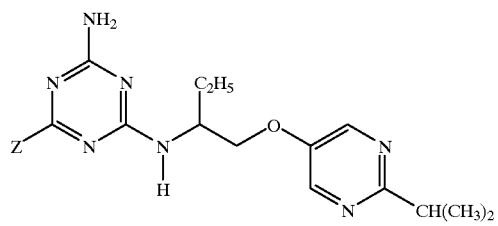
(I-98)

Here, Z has, for example, the meanings given above in group 1.

Using, for example, 1-(1-ethyl-3-phenyl-propyl)-biguanide and methyl trifluoro-acetate as starting materials, the course of the reaction in the process (a) according to the invention can be illustrated by the following equation:

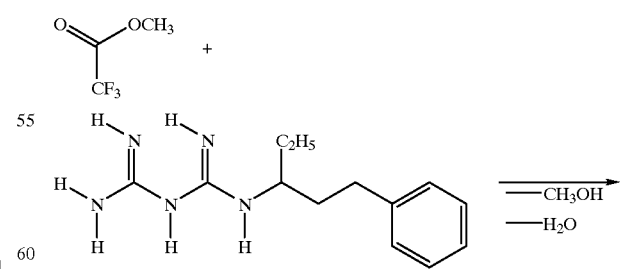

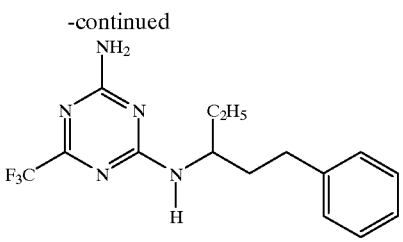

Using, for example, 2-chloro-4-(1-ethyl-3-phenyl-propylamino)-6-trifluoromethyl-1,3,5-triazine and ammonia as starting materials, the course of the reaction in the process (b) according to the invention can be illustrated by the following equation:

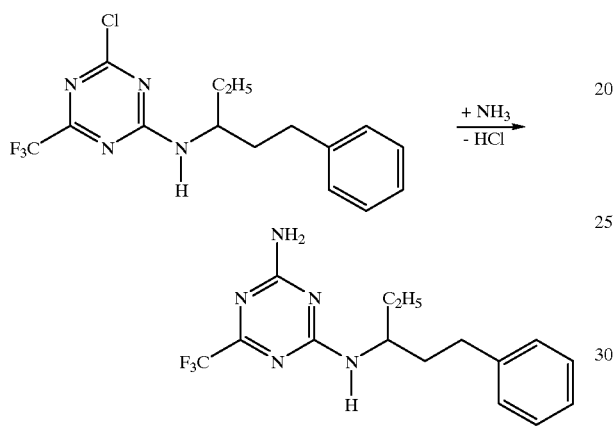

Using, for example, 2-amino-4-methoxy-6-trifluoromethyl-1,3,5-triazine and 3-phenyl-1-ethyl-propylamine as starting materials, the course of the reaction in the process (c) according to the invention can be illustrated by the following equation:

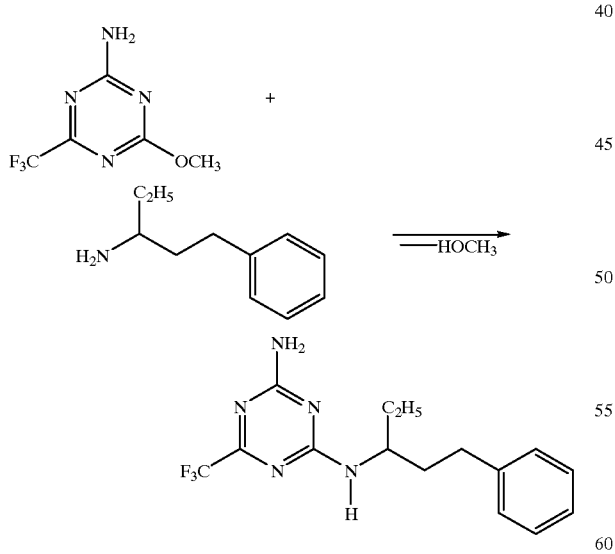

The formula (II) provides a general definition of the substituted biguanides to be used as starting materials in the process (a) according to the invention for preparing compounds of the formula (I). In the formula (11), $R^1$, $R^2$, A and Ar each preferably or in particular have those meanings which have already been mentioned above, in connection with the description of the compounds of the formula (I) according to the invention, as being preferred or as being particularly preferred for $R^1$, $R^2$, A and Ar. Examples of the substituted biguanides of the formula (II) which may be mentioned are:

1-(1-ethyl-3-phenyl-propyl)-, 1-(1-n-propyl-3-phenyl-propyl)-, 1-(1-i-propyl-3-phenyl-propyl)-, 1-(1-cyclopropyl-3-phenyl-propyl)-, 1-(1-ethyl-3-(2-fluoro-phenyl)-propyl)-, 1-(1-ethyl-3-(3-fluoro-phenyl)-propyl)-, 1-(1-ethyl-3-(4-fluoro-phenyl)-1-(1-ethyl-3-(2-chloro-phenyl)-propyl)-, 1-(1-ethyl-3-(3-chloro-phenyl)-propyl)-, 1-(1-ethyl-3-(4-chloro-phenyl)-propyl)-, 1-(1-ethyl-3-(2-bromo-phenyl)-propyl)-, 1-(1-ethyl-3-(3-bromo-phenyl)-propyl)-, 1-(1-ethyl-3-(4-bromo-phenyl)-propyl)-, 1-(1-ethyl-3-(2-nitro-phenyl)-propyl)-, 1-(1-ethyl-3-(3-nitro-phenyl)-propyl)-, 1-(1-ethyl-3 -(4-nitro-phenyl)-propyl)-, 1-(1-ethyl-3-(2-methyl-phenyl)-propyl)-, 1-(1-ethyl-3-(3-methyl-phenyl)-propyl)-, 1-(1-ethyl-3-(4-methyl-phenyl)-propyl)-, 1-(1-ethyl-3-(2-trifluoromethyl-phenyl)-propyl)-, 1-(1-ethyl-3-(3-trifluoromethyl-phenyl)-propyl)-, 1-(1-ethyl-3-(4-trifluoromethyl-phenyl)-propyl)-, 1-(1-ethyl-3-(2-methoxy-phenyl)-propyl)-, 1-(1-ethyl-3-(3-methoxy-phenyl)-propyl)-, 1-(1-ethyl-3-(4-methoxy-phenyl)-propyl)-, 1-(1-ethyl-3-(2-difluoromethoxy-phenyl)-propyl)-, 1-(1-ethyl-3-(2-difluoromethoxy-phenyl)-propyl)-, 1-(1-ethyl-3-(2-difluoromethoxy-phenyl)-propyl)-, 1-(1-ethyl-3-(2-trifluoromethoxy-phenyl)-propyl)-, 1-(1-ethyl-3-(3-trifluoromethoxyphenyl)-propyl), 1-(1-ethyl-3-(4-trifluoromethoxy-phenyl)-propyl)-, 1-(1-ethyl-3-(2-methoxycarbonyl-phenyl)-propyl)-, 1-(1-ethyl-3-(2-ethoxycarbonyl-phenyl)-propyl)-, 1-(1-ethyl-3-(4-methoxycarbonyl-phenyl)-propyl)-, 1-(1-ethyl-3-(4-ethoxycarbonylphenyl)-propyl)-, 1-(1-ethyl-3-(2-methylthio-phenyl)-propyl)-, 1-(1-ethyl-3-(4-methylthio-phenyl)-propyl)-, 1-(1-ethyl-3-(2-methylsulphinyl-phenyl)-propyl)-, 1-(1-ethyl-3-(4-methylsulphinyl-phenyl)-propyl)-, 1-(1-ethyl-3-(2-methylsulphonyl-phenyl)-propyl)-, 1-(1-ethyl-3-(4-methylsulphonyl-phenyl)-propyl)-, 1-(1-ethyl-3-(3,4-dichloro-phenyl)-propyl)-, 1-(1-ethyl-3-(2,4-dichloro-phenyl)-propyl)-, 1-(1-ethyl-3-(2,5-dichloro-phenyl)-propyl)-, 1-(1-ethyl-3-(2,6-dichloro-phenyl)-propyl)-, 1-(1-ethyl-3-(2,6-difluoro-phenyl)-propyl)-, 1-(1-ethyl-3-(2,5-difluoro-phenyl)-propyl)-, 1-(1-ethyl-3-(2,4-difluoro-phenyl)-propyl)-, 1-(1-ethyl-3-(3,4-difluoro-phenyl)-propyl)-, 1-(1-ethyl-3-(3,5-difluoro-phenyl)-propyl)-, 1-(1-ethyl-3-(2-fluoro-4-chlorophenyl)-propyl)-, 1-(1-ethyl-3-(4-fluoro-2-chloro-phenyl)-propyl)-, 1-(1-ethyl-3-(2,4-dimethyl-phenyl)-propyl)-, 1-(1-ethyl-3-(3,4-dimethyl-phenyl)-propyl)-, 1-(1-ethyl-3-(3,5-dimethyl-phenyl)-propyl)-, 1-(1-ethyl-3-(2,5-dimethyl-phenyl)-propyl)-, 1-(1-ethyl-3-(2-chloro-6-methyl-phenyl)-propyl)-, 1-(1-ethyl-3-(4-fluoro-2-methyl-phenyl)-propyl)-, 1-(1-ethyl-3-(2-fluoro-4-methyl-phenyl)-propyl)-, 1-(1-ethyl-3-(2-fluoro-5-methyl-phenyl)-propyl)-, 1-(1-ethyl-3-(5-fluoro-2-methyl-phenyl)-propyl)-, 1-(1-ethyl-3-thien-2-yl-propyl)-, 1-(1-ethyl-3-thien-3-yl-propyl)-, 1-(1-ethyl-3-pyridin-2-yl-propyl)-, 1-(1-ethyl-3-pyridin-3-yl-propyl)- and 1-(1-ethyl-3-pyridin-4-yl-propyl)-biguanide.

Suitable acid adducts of compounds of the formula (II) are their addition products with protic acids, such as, for example with hydrogen chloride, hydrogen bromide, sulphuric acid, methanesulphonic acid, benzenesulphonic acid and p-toluene-sulphonic acid.

The starting materials of the general formula (II) have hitherto not been disclosed in the literature; as novel substances, they also form part of the subject matter of the present application.

The novel substituted biguanides of the general formula (II) are obtained when substituted alkylamines of the general formula (VI),

(VI)

in which $R^1$, $R^2$, A and Ar are each as defined above —and/or acid adducts of compounds of the general formula (VI), such as, for example, the hydrochlorides—are reacted with cyanoguanidine ("dicyanodiamide") of the formula (VII)

(VII)

if appropriate in the presence of a reaction auxiliary, such as, for example, hydrogen chloride, and if appropriate in the presence of a diluent, such as, for example, n-decane or 1,2-dichloro-benzene, at temperatures between 100°C. and 200° C. (cf. EP 492615, Preparation Examples).

The substituted alkylamino compounds of the general formula (VI) required as precursors for this purpose are known and/or can be prepared by processes known per se (cf. J. Med. Chem. 10 (1967); 717–724; J. Am. Chem. Soc. 97 (1975), 6900–6901; Tetrahedron Lett. 35 (1994), 3745–3746; DE 3222152; DE 3221540; EP 355351; EP 601486; Preparation Examples).

The formula (III) provides a general definition of the alkoxycarbonyl compounds further to be used as starting materials in the process (a) according to the invention for preparing compounds of the formula (I). In the formula (III), Z preferably or in particular has that meaning which has already been mentioned above,. in connection with the description of the compounds of the formula (I) according to the invention, as being preferred or as being particularly preferred for Z; R' preferably represents alkyl having 1 to 4 carbon atoms, and in particular represents methyl or ethyl.

The starting materials of the formula (III) are known chemicals for synthesis.

The formula (IV) provides a general definition of the substituted triazines to be used as starting materials in the process (b) according to the invention for preparing compounds of the formula (I). In the formula (IV), $R^1$, $R^2$, A, Ar and Z each preferably or in particular have those meanings which have already been mentioned above, in connection with the description of the compounds of the formula (I) according to the invention, as being preferred or as being particularly preferred for $R^1$, $R^2$, A, Ar and Z; $X^1$ preferably represents fluorine, chlorine, bromine, methoxy or ethoxy, and in particular represents chlorine or methoxy.

Examples of the substituted triazines of the formula (IV) which may be mentioned are:

2-(1-ethyl-3-phenyl-propylamino)-, 2-(1-ethyl-3-(2-fluoro-phenyl)-propylamino)-, 2-(1-ethyl-3-(3-fluoro-phenyl)-propylamino)-, 2-(1-ethyl-3-(4-fluoro-phenyl)-propylamino)-, 2-(1ethyl-3-(2-chloro-phenyl)-propylamino)-, 2-(1-ethyl-3-(3-chloro-phenyl)-propylamino )-, 2-(1-ethyl-3-(4-chloro-phenyl)-propylamino)-, 2-(1-ethyl-3-(2-bromo-phenyl)-propylamino)-, 2-(1-ethyl-3-(3-bromo-phenyl)-propylamino)-, 2-(1-ethyl-3-(4-bromo-phenyl)-propylamino)-, 2-(1-ethyl-3-(2-nitro-phenyl)-propylamino)-, 2-(1-ethyl-3-(3-nitro-phenyl)-propylamino)-, 2-(1-ethyl-3-(4-nitro-phenyl)-propylamino)-, 2-(1-ethyl-3-(2-methyl-phenyl)-propylamino)-, 2-(1-ethyl-3-(3-methyl-phenyl)-propylamino)-, 2-(1-ethyl-3-(4-methyl-phenyl)-propylamino)-, 2-(1-ethyl-3-(2-trifluoromethyl-phenyl)-propylamino)-, 2-(1-ethyl-3-(3-trifluoromethylphenyl)-propylamino)-, 2-(1-ethyl-3-(4-trifluoromethyl-phenyl)-propylamino)-, 2-(1-ethyl-3-(2-methoxy-phenyl)-propylamino)-, 2-(1-ethyl-3-(3-methoxy-phenyl)-propylamino)-, 2-(1-ethyl-3-(4-methoxy-phenyl)-propylamino)-, 2-(1-ethyl-3-(2-difluoromethoxy-phenyl)-propylamino)-, 2-(1-ethyl-3-(2-difluoromethoxy-phenyl)-propylamino)-, 2-(1-ethyl-3-(2-difluoromethoxy-phenyl)-propylamino)-, 2-(1-ethyl-3-(2-trifluoromethoxy-phenyl)-propylamino)-, 1-(1-ethyl-3-(3-trifluoromethoxyphenyl)-propylamino)-, 2-(1-ethyl-3-(4-trifluoromethoxy-phenyl)-propylamino)-, 2-(1-ethyl-3-(2-methoxycarbonyl-phenyl)-propylamino)-, 2-(1-ethyl-3-(2-ethoxycarbonyl-phenyl)-propylamino)-, 2-(1-ethyl-3-(4-methoxycarbonyl-phenyl)-propylamino)-, 2-(1-ethyl-3-(4-ethoxycarbonyl-phenyl)-propylamino)-, 2-(1-ethyl-3-(2-methylthio-phenyl)-propylamino)-, 2-(1-ethyl-3-(4-methylthio-phenyl)-propylamino)-, 2(1-ethyl-3-(2-methylsulphinyl-phenyl)-propylamino)-, 2-(1-ethyl-3-(4-methylsulphinyl-phenyl)-propylamino)-, 2-(1-ethyl-3-(2-methylsulphonyl-phenyl)-propylamino)-, 2-(1-ethyl-3-(4-methylsulphonyl-phenyl)-propylamino)-, 2-(1-ethyl-3-(3,4-dichloro-phenyl)-propylamino)-, 2-(1-ethyl-3-(2,4-dichloro-phenyl)-propylamino)-, 2-(1-ethyl-3-(2,5-dichloro-phenyl)-propylamino)-, 2-(1-ethyl-3-(2,6-dichloro-phenyl)-propylamino)-, 2-(1-ethyl-3-(2,6-difluoro-phenyl)-propylamino)-, 2-(1-ethyl-3-(2,5-difluoro-phenyl)-propylamino)-, 2-(1-ethyl-3-(2,4-difluoro-phenyl)-propylamino)-, 2-(1-ethyl-3-(3,4-difluoro-phenyl)-propylamino)-, 2-(1-ethyl-3-(3,5-difluoro-phenyl)-propylamino)-, 2-(1-ethyl-3-(2-fluoro-4-chloro-phenyl)-propylamino)-, 2-(1-ethyl-3-(4-fluoro-2-chloro-phenyl)-propylamino)-, 2-(1-ethyl-3-(2,4-dimethyl-phenyl)-propylamino)-, 2-(1-ethyl-3-(3,4-dimethyl-phenyl)-propylamino)-, 2-(1-ethyl-3-(3,5-dimethyl-phenyl)-propylamino)-, 2-(1-ethyl-3-(2,5-dimethyl-phenyl)-propylamino)-, 2-(1-ethyl-3-(2-chloro-6-methyl-phenyl)-propylamino)-, 2-(1-ethyl-3-(4-fluoro-2-methyl-phenyl)-propylamino)-, 2-(1-ethyl-3-(2-fluoro-4-methyl-phenyl)-propylamino)-, 2-(1-ethyl-3-(2-fluoro-5-methyl-phenyl)-propylamino)-, 2-(1-ethyl-3-(5-fluoro-2-methyl-phenyl)-propylamino)-, 2-(1-ethyl-3-thien-2-yl-propylamino)-, ²-(1-ethyl-3-thien-3-yl-propylamino)-, 2-(1-ethyl-3-pyridin-2-yl-propylamino)-, 2-(1-ethyl-3-pyridin-3-yl-propylamino)- and 2-(1-ethyl-3-pyridin-4-yl-propylamino)- -4,6-dichloro-1,3,5-triazine;

2-(1-ethyl-3-phenyl-propylamino)-, 2-(1-ethyl-3-(2-fluoro-phenyl)-propylamino)-, 2-(1-ethyl-3-(3-fluorophenyl)-propylamino)-, 2-(1-ethyl-3-(4-fluoro-phenyl)-propylamino)-, 2-(1-ethyl-3-(2-chloro-phenyl)-propylamino)-, 2-(1-ethyl-3-(3-chlorophenyl)-propylamino)-, 2-(1-ethyl-3-(4-chloro-phenyl)-propylamino)-, 2-(1-ethyl-3-(2-bromo-phenyl)-propylamino)-, 2-(1-ethyl-3-(3-bromo-phenyl)-propylamino)-, 2-(1-ethyl-3-(4-bromo-phenyl)-propylamino)-, 2-(1-ethyl-3-(2-nitro-phenyl)-propylamino)-, 2-(1-ethyl-3-(3-nitro-phenyl)-propylamino)-, 2-(1-ethyl-3-(4-nitro-phenyl)-propylamino)-, 2-(1-ethyl-3-(2-methyl-phenyl)-propylamino)-, 2-(1-ethyl-3-(3-methyl-phenyl)-propylamino)-, 2-(1-ethyl-3-(4-methyl-phenyl)-propylamino)-, 2-(1-ethyl- 3-(2-trifluoromethyl-phenyl)-propylamino)-, 2-(1-ethyl-3-(3-trifluoromethylphenyl)-propylamino)-, 2-(1-ethyl-3-(4-trifluoromethyl-phenyl)-propylamino)-, 2-(1-ethyl-3-(2-methoxy-phenyl)-propylamino)-, 2-(1-ethyl-3-(3-methoxy-phenyl)-propylamino)-, 2-(1-ethyl-3-(4-methoxy-phenyl)-propylamino)-, 2-(1-ethyl-3-(2-difluoromethoxy-phenyl)-propylamino)-, 2-(1-ethyl-3-(2-difluoromethoxy-phenyl)-propylamino)-, 2-(1-ethyl-3-(2-difluoromethoxy-phenyl)-propylamino)-, 2-(1-ethyl-3-(2-trifluoromethoxy-phenyl)-propylamino)-, 1-(1-ethyl-3-(3-trifluoromethoxy-phenyl)-propylamino)-, 2-(1-ethyl-3-(4-trifluoromethoxy-phenyl)-propylamino)-, 2-(1-ethyl-3-(2-methoxycarbonyl-phenyl)-propylamino)-, 2-(1-ethyl-3-(2-ethoxy-carbonyl-phenyl)-propylamino)-, 2-(1-ethyl-3-(4-methoxycarbonyl-phenyl)-propylamino)-, 2-(1-ethyl-3-(4-ethoxycarbonyl-phenyl)-propylamino)-, 2-(1-ethyl-3-(2-methylthio-phenyl)-propylamino)-, 2-(1-ethyl-3-(4-methylthio-phenyl)-propylamino)-, 2-(1-ethyl-3-(2-methylsulphinyl-phenyl)-propylamino)-, 2-(1-ethyl-3-(4-methylsulphinyl-phenyl)-propylamino)-, 2-(1-ethyl-3-(2-methylsulphonyl-phenyl)propylamino)-, 2-(1-ethyl-3-(4-methylsulphonyl-phenyl)-propylamino)-, 2-(1-ethyl-3-(3,4-dichloro-phenyl)-propylamino)-, 2-(1-ethyl-3-(2,4-dichloro-phenyl)-propylamino)-, 2-(1-ethyl-3-(2,5-dichloro-phenyl)-propylamino)-, 2-(1-ethyl-3-(2,6-dichloro-phenyl)-propylamino)-, 2-(1-ethyl-3-(2,6-difluoro-phenyl)-propylamino)-, 2-(1-ethyl-3-(2,5-difluoro-phenyl)-propylamino)-, 2-(1-ethyl-3-(2,4-difluoro-phenyl)propylamino)-, 2-(1-ethyl-3-(3,4-difluoro-phenyl)-propylamino)-, 2-(1-ethyl-3-(3,5-difluoro-phenyl)-propylamino)-, 2-(-ethyl-3-(2-fluoro-4-chloro-phenyl)-propylamino)-, 2-(1-ethyl-3-(4-fluoro-2-chloro-phenyl)-propylamino)-, 2-(1-ethyl-3-(2,4-dimethyl-phenyl)-propylamino)-, 2-(1-ethyl-3-(3,4-dimethyl-phenyl)-propylamino)-, 2-(1-ethyl-3-(3,5-dimethyl-phenyl)-propylamino)-, 2-(1-ethyl-3-(2,5-dimethyl-phenyl)-propylamino)-, 2-(1-ethyl-3-(2-chloro-6-methyl-phenyl)-propylamino)-, 2-(-ethyl-3-(4-fluoro-2-methyl-phenyl)-propylamino)-, 2-(1-ethyl-3-(2-fluoro-4-methyl-phenyl)-propylamino)-, 2-(1-ethyl-3-(2-fluoro-5-methyl-phenyl)-propylamino)-, 2-(1-ethyl-3-(5-fluoro-2-methyl-phenyl)-propylamino)-, 2-(1-ethyl-3-thien-2-yl-propylamino)-, 2-(1-ethyl-3-thien-3-yl-propylamino)-, 2-(1-ethyl-3-pyridin-2-yl-propylamino)-, 2-(1-ethyl-3-pyridin-3-yl-propylamino)- and 2-(1-ethyl-3-pyridin-4-yl-propylamino)- -4-chloro-6-methyl-1,3,5-triazine;

2-(1-ethyl-3-phenyl-propylamino)-, 2-(1-ethyl-3-(2-fluoro-phenyl)-propylamino)-, 2-(1-ethyl-3-(3-fluoro-phenyl)-propylamino)-, 2-(1-ethyl-3-(4-fluoro-phenyl)-propylamino)-, 2-(1-ethyl-3-(2-chloro-phenyl)-propylamino)-, 2-(1-ethyl-3-(3-chlorophenyl)-propylamino)-, 2-(1-ethyl-3-(4-chloro-phenyl)-propylamino)-, 2-(1-ethyl-3-(2-bromo-phenyl)-propylamino)-, 2-(1-ethyl-3-(3-bromo-phenyl)-propylamino)-, 2-(1-ethyl-3-(4-bromo-phenyl)-propylamino)-, 2-(1-ethyl-3-(2-nitro-phenyl)-propylamino)-, 2-(1-ethyl-3-(3-nitro-phenyl)-propylamino)-, 2-(1-ethyl-3-(4-nitro-phenyl)-propylamino)-, 2-(1-ethyl-3-(2-methyl-phenyl)-propylamino)-, 2-(1-ethyl-3-(3-methyl-phenyl)-propylamino)-, 2-(1-ethyl-3-(4-methyl-phenyl)-propylamino)-, 2-(1-ethyl-3-(2-trifluoromethyl-phenyl)-propylamino)-, 2-(1-ethyl-3-(3-trifluoromethylphenyl)-propylamino)-, 2-(1-ethyl-3-(4-trifluoromethyl-phenyl)-propylamino)-, 2-(1-ethyl-3-(2-methoxy-phenyl)-propylamino)-, 2-(1-ethyl-3-(3-methoxy-phenyl)-propylamino)-, 2-(1-ethyl-3-(4-methoxy-phenyl)-propylamino)-, 2-(1-ethyl-3-(2-difluoromethoxy-phenyl)-propylamino)-, 2-(1-ethyl-3-(2-difluoromethoxy-phenyl)-propylamino)-, 2-(1-ethyl-3-(2-difluoromethoxy-phenyl)-propylamino)-, 2-(1-ethyl-3-(2-trifluoromethoxy-phenyl)-propylamino)-, 1-(1-ethyl-3-(3-trifluoromethoxy-phenyl)-propylamino)-, 2-(1-ethyl-3-(4-trifluoromethoxy-phenyl)-propylamino)-, 2-(1-ethyl-3-(2-methoxycarbonyl-phenyl)-propylamino)-, 2-(1-ethyl-3-(2-ethoxycarbonyl-phenyl)-propylamino)-, 2-(1-ethyl-3-(4-methoxycarbonyl-phenyl)-propylamino)-, 2-(1-ethyl-3-(4-ethoxycarbonyl-phenyl)-propylamino)-, 2-(1-ethyl-3-(2-methylthio-phenyl)-propylamino)-, 2-(1-ethyl-3-(4-methylthio-phenyl)-propylamino)-, 2-(1-ethyl-3-(2-methylsulphinyl-phenyl)-propylamino)-, 2-(1-ethyl-3-(4-methylsulphinyl-phenyl)-propylamino)-, 2-(1-ethyl-3-(2-methylsulphonyl-phenyl)-propylamino)-, 2-(1-ethyl-3-(4-methylsulphonyl-phenyl)-propylamino)-, 2-(1-ethyl-3-(3,4-dichloro-phenyl)-propylamino)-, 2-(1-ethyl-3-(2,4-dichloro-phenyl)-propylamino)-, 2-(1-ethyl-3-(2,5-dichloro-phenyl)-propylamino)-, 2-(1-ethyl-3-(2,6-dichloro-phenyl)-propylamino)-, 2-(1-ethyl-3-(2,6-difluoro-phenyl)-propylamino)-, 2-(1-ethyl-3-(2,5-difluoro-phenyl)-propylamino)-, 2-(1-ethyl-3-(2,4-difluoro-phenyl)-propylamino)-, 2-(1-ethyl-3-(3,4-difluoro-phenyl)-propylamino)-, 2-(1-ethyl-3-(3,5-difluoro-phenyl)-propylamino)-, 2-(1-ethyl-3-(2-fluoro-4-chloro-phenyl)-propylamino)-, 2-(-ethyl-3-(4-fluoro-2-chloro-phenyl)-propylamino)-, 2-(1-ethyl-3-(2,4-dimethyl-phenyl)-propylamino)-, 2-(1-ethyl-3-(3,4-dimethyl-phenyl)-propylamino)-, 2-(1-ethyl-3-(3,5-dimethyl-phenyl)-propylamino)-, 2-(1-ethyl-3-(2,5-dimethyl-phenyl)-propylamino)-, 2-(1-ethyl-3-(2-chloro-6-methylphenyl)-propylamino)-, 2-(1-ethyl-3-(4-fluoro-2-methyl-phenyl)-propylamino)-, 2-(1-ethyl-3-(2-fluoro-4-methylphenyl)-propylamino)-, 2-(1-ethyl-3-(2-fluoro-5-methyl-phenyl)-propylamino)-, 2-(1-ethyl-3-(5-fluoro-2-methyl-phenyl)-propylamino)-, 2-(1-ethyl-3-thien-2-yl-propylamino)- -4-chloro-6-trifluoromethyl-1,3,5-triazine;

2-(1-ethyl-3-thien-3-yl-propylamino)-, 2-(1-ethyl-3-pyridin-2-yl-propylamino)-, 2-(1-ethyl-3-pyridin-3-yl-propylamino)- and 2-(1-ethyl-3-pyridin-4-yl-propylamino)- -4-chloro-6-trifluoromethyl-1,3,5-triazine;

2-(1-ethyl-3-phenyl-propylamino)-, 2-(1-ethyl-3-(2-fluoro-phenyl)-propylamino)-, 2-(1-ethyl-3-(3-fluorophenyl)-propylamino)-, 2-(1-ethyl-3-(4-fluoro-phenyl)-propylamino)-, 2-(1-ethyl-3-(2-chloro-phenyl)-propylamino)-, 2-(1-ethyl-3-(3-chlorophenyl)-propylamino)-, 2-(1-ethyl-3-(4-chloro-phenyl)-propylamino)-, 2-(1-ethyl-3-(2-bromo-phenyl)-propylamino)-, 2-(1-ethyl-3-(3-bromo-phenyl)-propylamino)-, 2-(1-ethyl-3-(4-bromo-phenyl)-propylamino)-, 2-(1-ethyl-3-(2-nitro-phenyl)-propylamino)-, 2-(1-ethyl-3-(3-nitro-phenyl)-propylamino)-, 2-(1-ethyl-3-(4-nitro-phenyl)-propylamino)-, 2-(1-ethyl-3-(2-methyl-phenyl)-propylamino)-, 2-(1-ethyl-3-(3-methyl-phenyl)-propylamino)-, 2-(1-ethyl-3-(4-methyl-phenyl)-propylamino)-, 2-(1-ethyl-3-(2-trifluoromethyl-phenyl)-propylamino)-, 2-(1-ethyl-3-(3-trifluoromethyl-phenyl)-propylamino)-, 2-(1-ethyl-3-(4-trifluoromethyl-phenyl)-propylamino)-, 2-(1-ethyl-3-(2-methoxy-phenyl)-propylamino)-, 2-(1-ethyl-3-(3-methoxy-phenyl)-propylamino)-, 2-(1-ethyl-3-(4-methoxy-phenyl)-propylamino)-, 2-(1-ethyl-3-(2-difluoromethoxy-phenyl)-propylamino)-, 2-(1-ethyl-3-(2-difluoromethoxy-phenyl)-propylamino)-, 2-(1-ethyl-3-(2-difluoromethoxy-phenyl)-propylamino)-, 2-(1-ethyl-3-(2-trifluoromethoxy-phenyl)-propylamino)-, 1-(1-ethyl-3-(3-trifluoromethoxy-phenyl)-propylamino)-, 2-(1-ethyl-3-(4-trifluoromethoxy-phenyl)-propylamino)-, 2-(1-ethyl-3-(2-methoxycarbonyl-phenyl)-propylamino)-, 2-(1-ethyl-3-(2-ethoxycarbonyl-phenyl)-propylamino)-, 2-(1-ethyl-3-(4-methoxycarbonyl-phenyl)-propylamino)-, 2-(1-ethyl-3-(4-ethoxycarbonyl-phenyl)-propylamino)-, 2-(1-ethyl-3-(2-methylthio-phenyl)-propylamino)-, 2-(1-ethyl-3-(4-methylthio-phenyl)-propylamino)-, 2-(1-ethyl-3-(2-methylsulphinyl-phenyl)-propylamino)-, 2-(1-ethyl-3-(4-methylsulphinyl-phenyl)-propylamino)-, 2-(1-ethyl-3-(2-methylsulphonyl-phenyl)-propylamino)-, 2-(1-ethyl-3-(4-methylsulphonyl-phenyl)-propylamino)-, 2-(1-ethyl-3-(3,4-dichloro-phenyl)-propylamino)-, 2-(1-ethyl-3-(2,4-dichloro-phenyl)-propylamino)-, 2-(1-ethyl-3-(2,5-dichloro-phenyl)-propylamino)-, 2-(1-ethyl-3-(2,6-dichloro-phenyl)-propylamino)-, 2-(1-ethyl-3-(2,6-difluoro-phenyl)-propylamino)-, 2-(1-ethyl-3-(2,5-difluoro-phenyl)-propylamino)-, 2-(1-ethyl-3-(2,4-difluoro-phenyl)-propylamino)-, 2-(1-ethyl-3-(3,4-difluoro-phenyl)-propylamino)-, 2-(1-ethyl-3-(3,5-difluoro-phenyl)-propylamino)-, 2-(1-ethyl-3-(2-fluoro-4-chloro-phenyl)-propylamino)-, 2-(1-ethyl-3-(4-fluoro-2-chloro-phenyl)-propylamino)-, 2-(1-ethyl-3-(2,4-dimethyl-phenyl)-propylamino)-, 2-(1-ethyl-3-(3,4-dimethyl-phenyl)-propylamino)-, 2-(1-ethyl-3-(3,5-dimethyl-phenyl)-propylamino)-, 2-(1-ethyl-3-(2,5-dimethyl-phenyl)-propylamino)-, 2-(1-ethyl-3-(2-chloro-6-methylphenyl)-propylamino)-, 2-(1-ethyl-3-(4-fluoro-2-methyl-phenyl)-propylamino)-, 2-(1-ethyl-3-(2-fluoro-4-methyl-phenyl)-propylamino)-, 2-(1-ethyl-3-(2-fluoro-5-methyl-phenyl)-propylamino)-, 2-(1-ethyl-3-(5-fluoro-2-methyl-phenyl)-propylamino)-, 2-(1-ethyl-3-thien-2-yl-propylamino)-, 2-(1-ethyl-3-thien-3-yl-propylamino)-, 2-(1-ethyl-3-pyridin-2-yl-propylamino)-, 2-(1-ethyl-3-pyridin-3-yl-propylamino)- and 2-(1-ethyl-3-pyridin-4-yl-propylamino)- -4-chloro-6-(1-fluoro-ethyl)-1,3,5-triazine;

2-(1-ethyl-3-phenyl-propylamino)-, 2-(1-ethyl-3-(2-fluoro-phenyl)-propylamino)-, 2-(1-ethyl-3-(3-fluorophenyl)-propylamino)-, 2-(1-ethyl-3-(4-fluoro-phenyl)-propylamino)-, 2-(1-ethyl-3-(2-chloro-phenyl)-propylamino)-, 2-(1-ethyl-3-(3-chloro-phenyl)-propylamino)-, 2-(1-ethyl-3-(4-chloro-phenyl)-propylamino)-, 2-(1-ethyl-3-(2-bromo-phenyl)-propylamino)-, 2-(1-ethyl-3-(3-bromo-phenyl)-propylamino)-, 2-(1-ethyl-3-(4-bromo-phenyl)-propylamino)-, 2-(1-ethyl-3-(2-nitro-phenyl)-propylamino)-, 2-(1-ethyl-3-(3-nitro-phenyl)-propylamino)-, 2-(1-ethyl-3-(4-nitro-phenyl)-propylamino)-, 2-(1-ethyl-3-(2-methyl-phenyl)-propylamino)-, 2-(1-ethyl-3-(3-methyl-phenyl)-propylamino)-, 2-(1-ethyl-3-(4-methyl-phenyl)-propylamino)-, 2-(1-ethyl-3-(2-trifluoromethyl-phenyl)-propylamino)-, 2-(1-ethyl-3-(3-trifluoromethyl-phenyl)-propylamino)-, 2-(1-ethyl-3-(4-trifluoromethyl-phenyl)-propylamino)-, 2-(1-ethyl-3-(2-methoxy-phenyl)-propylamino)-, 2-(1-ethyl-3-(3-methoxy-phenyl)-propylamino)-, 2-(1-ethyl-3-(4-methoxy-phenyl)-propylamino)-, 2-(1-ethyl-3-(2-difluoromethoxy-phenyl)-propylamino)-, 2-(1-ethyl-3-(2-difluoromethoxy-phenyl)-propylamino)-, 2-(1-ethyl-3-(2-difluoromethoxy-phenyl)-propylamino)-, 2-(1-ethyl-3-(2-trifluoromethoxy-phenyl)-propylamino)-, 1-(1-ethyl-3-(3-trifluoromethoxyphenyl)-propylamino)-, 2-(1-ethyl-3-(4-trifluoromethoxy-phenyl)-propylamino)-, 2-(1-ethyl-3-(2-methoxycarbonyl-phenyl)-propylamino)-, 2-(1-ethyl-3-(2-ethoxycarbonyl-phenyl)-propylamino)-, 2-(1-ethyl-3-(4-methoxycarbonyl-phenyl)-propylamino)-, 2-(1-ethyl-3-(4-ethoxycarbonyl-phenyl)-propylamino)-, 2-(1-ethyl-3-(2-methylthio-phenyl)-propylamino)-, 2-(1-ethyl-3-(4-methylthio-phenyl)-propylamino)-, 2-(1-ethyl-3-(2-methylsulphinyl-phenyl)-propylamino)-, 2-(1-ethyl-3-(4-methylsulphinyl-phenyl)-propylamino)-, 2-(1-ethyl-3-(2-methylsulphonyl-phenyl)-propylamino)-, 2-(1-ethyl-3-(4-methylsulphonyl-phenyl)-propylamino)-, 2-(1-ethyl-3-(3,4-dichloro-phenyl)-propylamino)-, 2-(1-ethyl-3-(2,4-dichloro-phenyl)-propylamino)-, 2-(1-ethyl-3-(2,5-dichloro-phenyl)-propylamino)-, 2-(1-ethyl-3-(2,6-dichloro-phenyl)-propylamino)-, 2-(1-ethyl-3-(2,6-difluoro-phenyl)-propylamino)-, 2-(1-ethyl-3-(2,5-difluoro-phenyl)-propylamino)-, 2-(1-ethyl-3-(2,4-difluoro-phenyl)-propylamino)-, 2-(1-ethyl-3-(3,4-difluoro-phenyl)-propylamino)-, 2-(1-ethyl-3-(3,5-difluoro-phenyl)-propylamino)-, 2-(1-ethyl-3-(2-fluoro-4-chloro-phenyl)-propylamino)-, 2-(1-ethyl-3-(4-fluoro-2-chloro-phenyl)-propylamino)-, 2-(1-ethyl-3-(2,4-dimethyl-phenyl)-propylamino)-, 2-(1-ethyl-3-(3,4-dimethyl-phenyl)-propylamino)-, 2-(1-ethyl-3-(3,5-dimethyl-phenyl)-propylamino)-, 2-(1-ethyl-3-(2,5-dimethyl-phenyl)-propylamino)-, 2-(1-ethyl-3-(2-chloro-6-methyl-phenyl)-propylamino)-, 2-(1-ethyl-3-(4-fluoro-2-methyl-phenyl)-propylamino)-, 2-(1-ethyl-3-(2-fluoro-4-methyl-phenyl)-propylamino)-, 2-(1-ethyl-3-(2-fluoro-5-methyl-phenyl)-propylamino)-, 2-(1-ethyl-3-(5-fluoro-2-methyl-phenyl)-propylamino)-, 2-(1-ethyl-3-thien-2-yl-propylamino)-, 2-(1-ethyl-3-thien-3-yl-propylamino)-, 2-(1-ethyl-3-pyridin-2-yl-propylamino)-, 2-(1-ethyl-3-pyridin-3-yl-propylamino)- and 2-(1-ethyl-3-pyridin-4-yl-propylamino)- -4-chloro-6-(1-fluoro-1-methyl-ethyl)-1,3,5-triazine;

2-(1-ethyl-3-phenyl-propylamino)-, 2-(1-ethyl-3-(2-fluoro-phenyl)-propylamino)-, 2-(1-ethyl-3-(3-fluorophenyl)-propylamino)-, 2-(1-ethyl-3-(4-fluoro-phenyl)-propylamino)-, 2-(1-ethyl-3-(2-chloro-phenyl)-propylamino)-, 2-(1-ethyl-3-(3-chloro-phenyl)-propylamino)-, 2-(1-ethyl-3-(4-chloro-phenyl)-propylamino)-, 2-(1-ethyl-3-(2-bromo-phenyl)-propylamino)-, 2-(1-ethyl-3-(3-bromo-phenyl)-propylamino)-, 2-(1-ethyl-3-(4-bromo-phenyl)-propylamino)-, 2-(1-ethyl-3-(2-nitro-phenyl)-propylamino)-, 2-(1-ethyl-3-(3-nitro-phenyl)-propylamino)-, 2-(1-ethyl-3-(4-nitro-phenyl)-propylamino)-, 2-(1-ethyl-3-(2-methyl-phenyl)-propylamino)-, 2-(1-ethyl-3-(3-methyl-phenyl)-propylamino)-, 2-(1-ethyl-3-(4-methyl-phenyl)-propylamino)-, 2-(1-ethyl-3-(2-trifluoromethyl-phenyl)-propylamino)-, 2-(1-ethyl-3-(3-trifluoromethyl-phenyl)-propylamino)-, 2-(1-ethyl-3-(4-trifluoromethyl-phenyl)-propylamino)-, 2-(1-ethyl-3-(2-methoxy-phenyl)-propylamino)-, 2-(1-ethyl-3-(3-methoxy-phenyl)-propylamino)-, 2-(1-ethyl-3-(4-methoxy-phenyl)-propylamino)-, 2-(1-ethyl-3-(2-difluoromethoxy-phenyl)-propylamino)-, 2-(1-ethyl-3-(2-difluoromethoxy-phenyl)-propylamino)-, 2-(1-ethyl-3-(2-difluoromethoxy-phenyl)-propylamino)-, 2-(1-ethyl-3-(2-trifluoromethoxy-phenyl)-propylamino)-, 1-(1-ethyl-3-(3-trifluoromethoxy-phenyl)-propylamino)-, 2-(1-ethyl-3-(4-trifluoromethoxy-phenyl)-propylamino)-, 2-(1-ethyl-3-(2-methoxycarbonyl-phenyl)-propylamino)-, 2-(1-ethyl-3-(2-ethoxy-carbonyl-phenyl)-propylamino)-, 2-(1-ethyl-3-(4-methoxycarbonyl-phenyl)-propylamino)-, 2-(1-ethyl-3-(4-ethoxycarbonyl-phenyl)-propylamino)-, 2-(1-ethyl-3-(2-methylthio-phenyl)-propylamino)-, 2-(1-ethyl-3-(4-methylthio-phenyl)-propylamino)-, 2-(1-ethyl-3-(2-methylsulphinyl-phenyl)-propylamino)-, 2-(1-ethyl-3-(4-methylsulphinyl-phenyl)-propylamino)-, 2-(1-ethyl-3-(2-methylsulphonyl-phenyl)-propylamino)-, 2-(1-ethyl-3-(4-methylsulphonyl-phenyl)-propylamino)-, 2-(1-ethyl-3-(3,4-dichloro-phenyl)-propylamino)-, 2-(1-ethyl-3-(2,4-dichloro-phenyl)-propylamino)-, 2-(1-ethyl-3-(2,5-dichloro-phenyl)-propylamino)-, 2-(1-ethyl-3-(2,6-dichloro-phenyl)-propylamino)-, 2-(1-ethyl-3-(2,6-difluoro-phenyl)-propylamino)-, 2-(1-ethyl-3-(2,5-difluoro-phenyl)-propylamino)-, 2-(1-ethyl-3-(2,4-difluoro-phenyl)-propylamino)-, 2-(1-ethyl-3-(3,4-difluoro-phenyl)-propylamino)-, 2-(1-ethyl-3-(3,5-difluoro-phenyl)-propylamino)-, 2-(1-ethyl-3-(2-fluoro-4-chloro-phenyl)-propylamino)-, 2-(1-ethyl-3-(4-fluoro-2-chloro-phenyl)-propylamino)-, 2-(1-ethyl-3-(2,4-dimethyl-phenyl)-propylamino)-, 2-(1-ethyl-3-(3,4-dimethyl-phenyl)-propylamino)-, 2-(1-ethyl-3-(3,5-dimethyl-phenyl)-propylamino)-, 2-(1-ethyl-3-(2,5-dimethyl-phenyl)-propylamino)-, 2-(1-ethyl-3-(2-chloro-6-methyl-phenyl)-propylamino)-, 2-(1-ethyl-3-(4-fluoro-2-methyl-phenyl)-propylamino)-, 2-(1-ethyl-3-(2-fluoro-4-methyl-phenyl)-propylamino)-, 2-(1-ethyl-3-(2-fluoro-5-methyl-phenyl)-propylamino)-, 2-(1-ethyl-3-(5-fluoro-2-methyl-phenyl)-propylamino)-, 2-(1-ethyl-3-thien-2-yl-propylamino)-, 2-(1-ethyl-3-thien-3-yl-propylamino)-, 2-(1-ethyl-3-pyridin-2-yl-propylamino)-, 2-(1-ethyl-3-pyridin-3-yl-propylamino)- and 2-(1-ethyl-3-pyridin-4-yl-propylamino)- -4-chloro-6-methoxy-1,3,5-triazine;

2-(1ethyl-3-phenyl-propylamino)-, 2-(1-ethyl-3-(2-fluoro-phenyl)-propylamino)-, 2-(1-ethyl-3-(3-fluoro-phenyl)-propylamino)-, 2-(1-ethyl-3-(4-fluoro-phenyl)-propylamino)-, 2-(1-ethyl-3-(2-chloro-phenyl)-propylamino)-, 2-(1-ethyl-3-(2-chloro-phenyt)-propylamino)-, 2-(1-ethyl-3-(3-chlorophenyl)-propylamino)-, 2-(1-ethyl-3-(4-chloro-phenyl)-propylamino)-, 2-(1-ethyl-3-(2-bromo-phenyl)-propylamino)-, 2-(1-ethyl-3-(3-bromo-phenyl)-propylamino)-, 2-(1-ethyl-3-(4-bromo-phenyl)-propylamino)-, 2-(1-ethyl-3-(2-nitro-phenyl)-propylamino)-, 2-(1-ethyl-3-(3-nitro-phenyl)-propylamino)-, 2-(.-ethyl-3-(4-nitro-phenyl)-propylamino)-, 2-(1-ethyl-3-(2-methyl-phenyl)-propylamino)-, 2-(1-ethyl-3-(3-methyl-phenyl)-propylamino)-, 2-(1-ethyl-3-(4-methyl-phenyl)-propylamino)-, 2-(1-ethyl-3-(2-trifluoromethyl-phenyl)-propylamino)-, 2-(1-ethyl-3-(3-trifluoromethyl-phenyl)-propylamino)-, 2-(1-ethyl-3-(4-trifluoromethyl-phenyl)-propylamino)-, 2-(1-ethyl-3-(2-methoxy-phenyl)-propylamino)-, 2-(1-ethyl-3-(3-methoxy-phenyl)-propylamino)-, 2-(1-ethyl-3-(4-methoxy-phenyl)-propylamino)-, 2-(1-ethyl-3-(2-difluoromethoxy-phenyl)-propylamino)-, 2-(1-ethyl-3-(2-difluoromethoxy-phenyl)-propylamino)-, 2-(1-ethyl-3-(2-difluoromethoxy-phenyl)-propylamino)-, 2-(1-ethyl-3-(2-trifluoromethoxy-phenyl)-propylamino)-, 1-(1-ethyl-3-(3-trifluoromethoxy-phenyl)-propylamino)-, 2-(1-ethyl-3-(4-trifluoromethoxy-phenyl)-propylamino)-, 2-(1-ethyl-3-(2-methoxycarbonyl-phenyl)-propylamino)-, 2-(1-ethyl-3-(2-ethoxy-carbonyl-phenyl)-propylamino)-, 2-(1-ethyl-3-(4-methoxycarbonyl-phenyl)-propylamino)-, 2-(1-ethyl-3-(4-ethoxycarbonyl-phenyl)-propylamino)-, 2-(1-ethyl-3-(2-methylthio-phenyl)-propylamino)-, 2-(1-ethyl-3-(4-methylthio-phenyl)-propylamino)-, 2-(1-ethyl-3-(2-methylsulphinyl-phenyl)-propylamino)-, 2-(1-ethyl-3-(4-methylsulphinyl-phenyl)-propylamino)-, 2-(1-ethyl-3-(2-methylsulphonyl-phenyl)-propylamino)-, 2-(1-ethyl-3-(4-methylsulphonyl-phenyl)-propylamino)-, 2-(1-ethyl-3-(3,4-dichloro-phenyl)-propylamino)-, 2-(1-ethyl-3-(2,4-dichloro-phenyl)-propylamino)-, 2-(1-ethyl-3-(2,5-dichloro-phenyl)-propylamino)-, 2-(1-ethyl-3-(2,6-dichloro-phenyl)-propylamino)-, 2-(1-ethyl-3-(2,6-difluoro-phenyl)-propylamino)-, 2-(1-ethyl-3-(2,5-difluoro-phenyl)-propylamino)-, 2-(1-ethyl-3-(2,4-difluoro-phenyl)-propylamino)-, 2-(1-ethyl-3-(3,4-difluoro-phenyl)-propylamino)-, 2-(1-ethyl-3-(3,5-difluoro-phenyl)-propylamino)-, 2-(1-ethyl-3-(2-fluoro-4-chloro-phenyl)-propylamino)-, 2-(1-ethyl-3-(4-fluoro-2-chloro-phenyl)-propylamino)-, 2-(1-ethyl-3-(2,4-dimethyl-phenyl)-propylamino)-, 2-(1-ethyl-3-(3,4-dimethyl-phenyl)-propylamino)-, 2-(1-ethyl-3-(3,5-dimethyl-phenyl)-propylamino)-, 2-(1-ethyl-3-(2,5-dimethyl-phenyl)-propylamino)-, 2-(1-ethyl-3-(2-chloro-6-methylphenyl)-propylamino)-, 2-(1-ethyl-3-(4-fluoro-2-methyl-phenyl)-propylamino)-, 2-(1-ethyl-3-(2-fluoro-4-methyl-phenyl)-propylamino)-, 2-(1-ethyl-3-(2-fluoro-5-methyl-phenyl)-propylamino)-, 2-(1-ethyl-3-(5-fluoro-2-methyl-phenyl)-propylamino)-, 2-(1-ethyl-3-thien-2-yl-propylamino)-, 2-(1-ethyl-3-thien-3-yl-propylamino)-, 2-(1-ethyl-3-pyridin-2-yl-propylamino)-, 2-(1-ethyl-3-pyridin-3-yl-propylamino)- and 2-(1-ethyl-3-pyridin-4-yl-propylamino)- -4-chloro-6-(2,2,2-trifluoro-ethoxy)-1,3,5-triazine;

2-(1-ethyl-3-phenyl-propylamino)-, 2-(1-ethyl-3-(2-fluoro-phenyl)-propylamino)-, 2-(1-ethyl-3-(3-fluoro-phenyl)-propylamino)-, 2-(1-ethyl-3-(4-fluoro-phenyl)-propylamino)-, 2-(1-ethyl-3-(2-chlorophenyl)-propylamino)-, 2-(1-ethyl-3-(3-chloro-phenyl)-propylamino)-, 2-(1-ethyl-3-(4-chloro-phenyl)-propylamino)-, 2-(1-ethyl-3-(2-bromo-phenyl)-propylamino)-, 2-(1-ethyl-3-(3-bromo-phenyl)-propylamino)-, 2-(1-ethyl-3-(4-bromo-phenyl)-propylamino)-, 2-(1-ethyl-3-(2-nitro-phenyl)-propylamino)-, 2-(1-ethyl-3-(3-nitro-phenyl)-propylamino)-, 2-(1-ethyl-3-(4-nitro-phenyl)-propylamino)-, 2-(1-ethyl-3-(2-methyl-phenyl)-propylamino)-, 2-(1-ethyl-3-(3-methyl-phenyl)-propylamino)-, 2-(1-ethyl-3-(4-methyl-phenyl)-propylamino)-, 2-(1-ethyl-3-(2-trifluoromethyl-phenyl)-propylamino)-, 2-(1-ethyl-3-(3-trifluoromethyl-phenyl)-propylamino)-, 2-(1-ethyl-3-(4-trifluoromethyl-phenyl)-propylamino)-, 2-(1-ethyl-3-(2-methoxy-phenyl)-propylamino)-, 2-(1-ethyl-3-(3-methoxy-phenyl)-propylamino)-, 2-(1-ethyl-3-(4-methoxy-phenyl)-propylamino)-, 2-(1-ethyl-3-(2-difluoromethoxy-phenyl)-propylamino)-, 2-(1-ethyl-3-(2-difluoromethoxy-phenyl)-propylamino)-, 2-(1-ethyl-3-(2-difluoromethoxy-phenyl)-propylamino)-, 2-(1-ethyl-3-(2-trifluoromethoxy-phenyl)-propylamino)-, 1-(1-ethyl-3-(3-trifluoromethoxy-phenyl)-propylamino)-, 2-(1-ethyl-3-(4-trifluoromethoxy-phenyl)-propylamino)-, 2-(1-ethyl-3-(2-methoxycarbonyl-phenyl)-propylamino)-, 2-(1-ethyl-3-(2-ethoxy-carbonyl-phenyl)-propylamino)-, 2-(1-ethyl-3-(4-methoxycarbonyl-phenyl)-propylamino)-, 2-(1-ethyl-3-(4-ethoxycarbonyl-phenyl)-propylamino)-, 2-(1-ethyl-3-(2-methylthio-phenyl)-propylamino)-, 2-(1-ethyl-3-(4-methylthio-phenyl)-propylamino)-, 2-(1-ethyl-3-(2-methylsulphinyl-phenyl)-propylamino)-, 2-(1-ethyl-3-(4-methylsulphinyl-phenyl)-propylamino)-, 2-(1-ethyl-3-(2-methylsulphonyl-phenyl)-propylamino)-, 2-(1-ethyl-3-(4-methylsulphonyl-phenyl)-propylamino)-, 2-(1-ethyl-3-(3,4-dichloro-phenyl)-propylamino)-, 2-(1-ethyl-3-(2,4-dichloro-phenyl)-propylamino)-, 2-(1-ethyl-3-(2,5-dichloro-phenyl)-propylamino)-, 2-(1-ethyl-3-(2,6-dichloro-phenyl)-propylamino)-, 2-(1-ethyl-3-(2,6-difluoro-phenyl)-propylamino)-, 2-(1-ethyl-3-(2,5-difluoro-phenyl)-propylamino)-, 2-(1-ethyl-3-(2,4-difluoro-phenyl)-propylamino)-, 2-(1-ethyl-3-(3,4-difluoro-phenyl)-propylamino)-, 2-(1-ethyl-3-(3,5-difluoro-phenyl)-propylamino)-, 2-(1-ethyl-3-(2-fluoro-4-chloro-phenyl)-propylamino)-, 2-(1-ethyl-3-(4-fluoro-2-chloro-phenyl)-propylamino)-, 2-(1-ethyl-3-(2,4-dimethyl-phenyl)-propylamino)-, 2-(1-ethyl-3-(3,4-dimethyl-phenyl)-propylamino)-, 2-(1-ethyl-3-(3,5-dimethyl-phenyl)-propylamino)-, 2-(1-ethyl-3-(2,5-dimethyl-phenyl)-propylamino)-, 2-(1-ethyl-3-(2-chloro-6-methylphenyl)-propylamino)-, 2-(1-ethyl-3-(4-fluoro-2-methyl-phenyl)-propylamino)-, 2-(1-ethyl-3-(2-fluoro-4-methyl-phenyl)-propylamino)-, 2-(1-ethyl-3-(2-fluoro-5-methyl-phenyl)-propylamino)-, 2-(1-ethyl-3-(5-fluoro-2-methyl-phenyl)-propylamino)-, 2-(1-ethyl-3-thien-2-yl-propylamino)-, 2-(1-ethyl-3-thien-3-yl-propylamino)-, 2-(1-ethyl-3-pyridin-2-yl-propylamino)-, 2-(1-ethyl-3-pyridin-3-yl-propylamino)- and 2-(1-ethyl-3-pyridin-4-yl-propylamino)- -4-chloro-6-methylthio-1,3,5-triazine;

2-(1-ethyl-3-phenyl-propylamino)-, 2-(1-ethyl-3-(2-fluoro-phenyl)-propylamino)-, 2-(1-ethyl-3-(3-fluoro-phenyl)-propylamino)-, 2-(1-ethyl-3-(4-fluoro-phenyl)-propylamino)-, 2-(1-ethyl-3-(2-chloro-phenyl)-propylamino)-, 2-(1-ethyl-3-(3-chlorophenyl)-propylamino)-, 2-(1-ethyl-3-(4-chloro-phenyl)-propylamino)-, 2-(1-ethyl-3-(2-bromo-phenyl)-propylamino)-, 2-(1-ethyl-3-(3-bromo-phenyl)-propylamino)-, 2-(1-ethyl-3-(4-bromo-phenyl)-propylamino)-, 2-(1-ethyl-3-(2-nitro-phenyl)-propylamino)-, 2-(1-ethyl-3-(3-nitro-phenyl)-propylamino)-, 2-(1-ethyl-3-(4-nitro-phenyl)-propylamino)-, 2-(1-ethyl-3-(2-methyl-phenyl)-propylamino)-, 2-(1-ethyl-3-(3-methyl-phenyl)-propylamino)-, 2-(1-ethyl-3-(4-methyl-phenyl)-propylamino)-, 2-(1-ethyl-3-(2-trifluoromethyl-phenyl)-propylamino)-, 2-(1-ethyl-3-(3-trifluoromethyl-phenyl)-propylamino)-, 2-(1-ethyl-3-(4-trifluoromethyl-phenyl)-propylamino)-, 2-(1-ethyl-3-(2-methoxy-phenyl)-propylamino)-, 2-(1-ethyl-3-(3-methoxy-phenyl)-propylamino)-, 2-(1-ethyl-3-(4-methoxy-phenyl)-propylamino)-, 2-(1-ethyl-3-(2-difluoromethoxy-phenyl)-propylamino)-, 2-(1-ethyl-3-(2-difluoromethoxy-phenyl)-propylamino)-, 2-(1-ethyl-3-(2-difluoromethoxy-phenyl)-propylamino)-, 2-(1-ethyl-3-(2-trifluoromethoxy-phenyl)-propylamino)-, 1-(1-ethyl-3-(3-trifluoromethoxy-phenyl)-propylamino)-, 2-(1-ethyl-3-(4-trifluoromethoxy-phenyl)-propylamino)-, 2-(1-ethyl-3-(2-methoxycarbonyl-phenyl)-propylamino)-, 2-(1-ethyl-3-(2-ethoxy-carbonyl-phenyl)-propylamino)-, 2-(1-ethyl-3-(4-methoxycarbonyl-phenyl)-propylamino)-, 2-(1-ethyl-3-(4-ethoxycarbonyl-phenyl)-propylamino)-, 2-(1-ethyl-3-(2-methylthio-phenyl)-propylamino)-, 2-(1-ethyl-3-(4-methylthio-phenyl)-propylamino)-, 2-(1-ethyl-3-(2-methylsulphinyl-phenyl)-propylamino)-, 2-(1-ethyl-3-(4-methylsulphinyl-phenyl)-propylamino)-, 2-(1-ethyl-3-(2-methylsulphonyl-phenyl)-propylamino)-, 2-(1-ethyl-3-(4-methylsulphonyl-phenyl)-propylamino)-, 2-(1-ethyl-3-(3,4-dichloro-phenyl)-propylamino)-, 2-(1-ethyl-3-(2,4-dichloro-phenyl)-propylamino)-, 2-(1-ethyl-3-(2,5-dichloro-phenyl)-propylamino)-, 2-(1-ethyl-3-(2,6-dichloro-phenyl)-propylamino)-, 2-(1-ethyl-3-(2,6-difluoro-phenyl)-propylamino)-, 2-(1-ethyl-3-(2,5-difluoro-phenyl)-propylamino)-, 2-(1-ethyl-3-(2,4-difluoro-phenyl)-propylamino)-, 2-(1-ethyl-3-(3,4-difluoro-phenyl)-propylamino)-, 2-(1-ethyl-3-(3,5-difluoro-phenyl)-propylamino)-, 2-(1-ethyl-3-(2-fluoro-4-chloro-phenyl)-propylamino)-, 2-(1-ethyl-3-(4-fluoro-2-chloro-phenyl)-propylamino)-, 2-(1-ethyl-3-(2,4-dimethyl-phenyl)-propylamino)-, 2-(1-ethyl-3-(3,4-dimethyl-phenyl)-propylamino)-, 2-(1-ethyl-3-(3,5-dimethyl-phenyl)-propylamino)-, 2-(1-ethyl-3-(2,5-dimethyl-phenyl)-propylamino)-, 2-(1-ethyl-3-(2-chloro-6-methylphenyl)-propylamino)-, 2-(1-ethyl-3-(4-fluoro-2-methyl-phenyl)-propylamino)-, 2-(1-ethyl-3-(2-fluoro-4-methyl-phenyl)-propylamino)-, 2-(1-ethyl-3-(2-fluoro-5-methyl-phenyl)-propylamino)-, 2-(1-ethyl-3-(5-fluoro-2-methyl-phenyl)-propylamino)-, 2-(1-ethyl-3-thien-2-yl-propylamino)-, 2-(1-ethyl-3-thien-3-yl-propylamino)-, 2-(1-ethyl-3-pyridin-2-yl-propylamino)-, 2-(1-ethyl-3-pyridin-3-yl-propylamino)- and 2-(1-ethyl-3-pyridin-4-yl-propylamino)- -4-chloro-6-methylsulphinyl-1,3,5-triazine;

2-(1-ethyl-3-phenyl-propylamino)-, 2-(1-ethyl-3-(2-fluoro-phenyl)-propylamino)-, 2-(1-ethyl-3-(3-fluoro-phenyl)-propylamino)-, 2-(1-ethyl-3-(4-fluoro-phenyl)-propylamino)-, 2-(1-ethyl-3-(2-chloro-phenyl)-propylamino)-, 2-(1-ethyl-3-(3-chlorophenyl)-propylamino)-, 2-(1-ethyl-3-(4-chloro-phenyl)-propylamino)-, 2-(1-ethyl-3-(2-bromo-phenyl)-propylamino)-, 2-(1-ethyl-3-(3-bromo-phenyl)-propylamino)-, 2-(1-ethyl-3-(4-bromo-phenyl)-propylamino)-, 2-(1-ethyl-3-(2-nitro-phenyl)-propylamino)-, 2-(1-ethyl-3-(3-nitro-phenyl)-propylamino)-, 2-(1-ethyl-3-(4-nitro-phenyl)-propylamino)-, 2-(1-ethyl-3-(2-methyl-phenyl )-propylamino)-, 2-(1-ethyl-3-(3-methyl-phenyl )-propylamino )-, 2-(1-ethyl-3-(4-methyl-phenyl)-propylamino)-, 2-(1-ethyl-3-(2-trifluoromethyl-phenyl)-propylamino)-, 2-(11-ethyl-3-(3-trifluoromethyl-phenyl)-propylamino)-, 2-(1-ethyl-3(4-trifluoromethyl-phenyl)-propylamino)-, 2-(1-ethyl-3-(2-methoxy-phenyl)-propylamino)-, 2-(1-ethyl-3-(3-methoxy-phenyl)-propylamino)-, 2-(1-ethyl-3-(4-methoxy-phenyl)-propylamino)-, 2-(1-ethyl-3-(2-difluoromethoxy-phenyl)-propylamino)-, 2-(1-ethyl-3-(2-difluoromethoxy-phenyl)-propylamino)-, 2-(1-ethyl-3-(2-difluoromethoxy-phenyl)-propylamino)-, 2-(1-ethyl-3-(2-trifluoromethoxy-phenyl)-propylamino)-, 1-(1-ethyl-3-(3-trifluoromethoxy-phenyl)-propylamino)-, 2-(1-ethyl-3-(4-trifluoromethoxy-phenyl)-propylamino)-, 2-(1-ethyl-3-(2-methoxycarbonyl-phenyl)-propylamino)-, 2-(1-ethyl-3-(2-ethoxy-carbonyl-phenyl)-propylamino)-, 2-(1-ethyl-3-(4-methoxycarbonyl-phenyl)-propylamino)-, 2-(1-ethyl-3-(4-ethoxy-carbonyl-phenyl)-propylamino)-, 2-(1-ethyl-3-(2-methylthio-phenyl)-propylamino)-, 2-(1-ethyl-3-(4-methylthio-phenyl)-propylamino), 2-(1-ethyl-3-(2-methylsulphinyl-phenyl)-propylamino)-, 2-(1-ethyl-3-(4-methylsulphinyl-phenyl)-propylamino)-, 2-(1-ethyl-3-(2-methylsulphonyl-phenyl)-propylamino)-, 2-(1-ethyl-3-(4-methylsulphonyl-phenyl)-propylamino)-, 2-(1-ethyl-3-(3,4-dichloro-phenyl)-propylamino)-, 2-(1-ethyl-3-(2,4-dichloro-phenyl)-propylamino)-, 2-(1-ethyl-3-(2,5-dichloro-phenyl)-propylamino)-, 2-(1-ethyl-3-(2,6-dichloro-phenyl)-propylamino)-, 2-(1-ethyl-3-(2,6-difluoro-phenyl)-propylamino)-, 2-(1-ethyl-3-(2,5-difluoro-phenyl)-propylamino)-, 2-(1-ethyl-3-(2,4-difluoro-phenyl)-propylamino)-, 2-(1-ethyl-3-(3,4-difluoro-phenyl)-propylamino)-, 2-(1-ethyl-3-(3,5-difluoro-phenyl)-propylamino)-, 2-(1-ethyl-3-(2-fluoro-4-chloro-phenyl)-propylamino)-, 2-(1-ethyl-3-(4-fluoro-2-chloro-phenyl)-propylamino)-, 2-(1-ethyl-3-(2,4-dimethyl-phenyl)-propylamino)-, 2-(1-ethyl-$^3$-(3,4-dimethyl-phenyl)-propylamino)-, 2-(1-ethyl-3-(3,5-dimethyl-phenyl)-propylamino)-, 2-(1-ethyl-3-(2,5-dimethyl-phenyl)-propylamino)-, 2-(1-ethyl-3-(2-chloro-6-methylphenyl)-propylamino)-, 2-(1-ethyl-3-(4-fluoro-2-methyl-phenyl)-propylamino)-, 2-(1-ethyl-3-(2-fluoro-4-methyl-phenyl)-propylamino)-, 2-(1-ethyl-3-(2-fluoro-5-methyl-phenyl)-propylamino)-, 2-(1-ethyl-3-(5-fluoro-2-methyl-phenyl)-propylamino)-, 2-(1-ethyl-3-thien-2-yl-propylamino)-, 2-(1-ethyl-3-thien-3-yl-propylamino)-, 2-(1-ethyl-3-pyridin-2-yl-propylamino)-, 2-(1-ethyl-3-pyridin-3-yl-propylamino)- and 2-(1-ethyl-3-pyridin-4-yl-propylamino)- -4-chloro-6-methylsulphonyl-1,3,5-triazine.

The starting materials of the general formula (IV) have hitherto not been disclosed in the literature; as novel substances, they also form part of the subject-matter of the present application.

The novel substituted triazines of the general formula (IV) are obtained when triazines of the general formula (VIII)

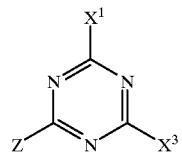

(VIII)

in which
X$^1$ and Z are each as defined above and
X$^3$ represents halogen
are reacted with substituted alkylamines of the general formula (VI)

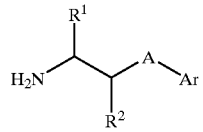

(VI)

in which
R$^1$, R$^2$, A and Ar are each as defined above,
if appropriate in the presence of an acid acceptor, such as, for example, ethyldiisopropylamine, and if appropriate in the presence of a diluent, such as, for example, tetrahydrofuran or dioxane, at temperatures between –50° C. and +50° C. (cf. the Preparation Examples).

The formula (V) provides a general definition of the substituted triazines to be used as starting materials in the process (c) according to the invention for preparing compounds of the formula (I). In the formula (V), Z preferably or in particular has that meaning which has already been mentioned above, in connection with the description of the compounds of the formula (I) according to the invention, as being preferred or as being particularly preferred for that; X$^2$ preferably represents fluorine, chlorine, bromine, methoxy or ethoxy, and in particular represents chlorine or methoxy.

The starting materials of the general formula (V) are known and/or can be prepared by processes known per se (cf. WO 95/11237).

The formula (VI) provides a general definition of the substituted alkylamines further to be used as starting materials in the process (c) according to the invention. In the formula (VI), R$^1$, R$^2$, A and Ar each preferably or in particular have those meanings which have already been mentioned above, in connection with the description of the compounds of the formula (IV) according to the invention, as being preferred or as being particularly preferred for R$^1$, R$^2$, A and Ar.

The starting materials of the general formula (VI) are known and/or can be prepared by processes known per se (cf. DE 3426919; DE 4000610; DE 4332738, EP 320898; EP 443606; Tetrahedron: Asymmetry 5 (1994), 817–820; Tetrahedron Lett. 29 (1988), 223–224; loc. cit. 36 (1995), 3917–3920; Preparation Examples).

If appropriate, the processes according to the invention for preparing the compounds of the formula (1) are carried out using a reaction auxiliary. Suitable reaction auxiliaries for the processes (a), (b) and (c) are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyl-diisopropylmine, N,N-dimethyl-cyclohexylamine, dicyclohexylamine, ethyl-dicyclohexylamine, N,N-dimethylaniline, N,N-dimethyl-benzylamine, pyridine, 2-methyl-, 3-methyl-, 4-ethyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo-[2,2,2]-octane (DABCO), 1,5-diazabicyclo[4,3,0]-non-5-ene (DBN), or 1,8-diazabicyclo[5,4,0]-undec-7-ene (DBU).

Suitable diluents for carrying out the processes (a), (b) and (c) according to the invention are especially inert organic solvents. These include in particular aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl or diethyl ether; ketones, such as methyl isopropyl ketone or methyl isobutyl ketone; nitriles, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters, such as methyl acetate or ethyl acetate, sulphoxides, such as dimethyl sulphoxide; alcohols, such as methanol, ethanol, n- or i-propanol, ethylene glycol monomethyl ether, ethylene glycol monoethyl ether, diethylene glycol monomethyl ether, diethylene glycol monoethyl ether, mixtures thereof with water or pure water.

In the practice of the processes (a), (b) and (c) according to the invention, the reaction temperatures can be varied over a relatively wide range. Generally, the reaction is carried out at temperatures between 0° C. and 300° C., preferably between 10° C. and 250° C.

The processes (a), (b) and (c) according to the invention are generally carried out at atmospheric pressure. However, it is also possible to carry out the processes according to the invention under elevated or reduced pressure—generally between 0.1 bar and 10 bar.

In the practice of the processes according to the invention, the starting materials are generally employed in approximately equimolar amounts. However, it is also possible to use a relatively large excess of one of the components. The reaction is generally carried out in a suitable diluent in the presence of a reaction auxiliary, and the reaction mixture is generally stirred for several hours at the temperature required. Work-up is carried out by conventional methods (cf. the Preparation Examples).

The active compounds according to the invention can be used as defoliants, desiccants, haulm killers and, especially, as weed-killers. By weeds in the broadest sense, there are to be understood all plants which grow in locations where they are undesirable. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera and Phalaris.

Monocotyledonous crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and railway tracks, and on paths and squares with or without tree plantings. Equally, the compounds can be employed for controlling weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture land, and for the selective control of weeds in annual cultures.

The compounds of the formula (I) according to the invention are suitable in particular for selectively controlling monocotyledonous and dicotyledonous weeds in monocotyledonous and dikotyledonous crops, both pre-emergence and post-emergence.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersing agents and/or foam-forming agents.

If the extender used is water, it is also possible to employ for example organic solvents as auxiliary solvents. Essentially, suitable liquid solvents are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-forming agents are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersing agents are: for example lignin-sulphite waste liquors and methylcellulose.

Tackifiers such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are known herbicides, for example acetochlor, acifluorfen(-sodium), aclonifen, alachlor, alloxydim(-sodium), ametryne, amidochlor, amidosulfuron, asulam, atrazine, azimsulfuron, benazolin, benfuiresate, bensulfuiron (-methyl), bentazon, benzofenap, benzoylprop(-ethyl), bialaphos, bifenox, bromobutide, bromofenoxim, bromoxynil, butachlor, butylate, cafenstrole, carbetamide, chlomethoxyfen, chloramben, chloridazon, chlorimuron(-ethyl), chlornitrofen, chlorsulfuron, chlortoluron, cinmethylin, cinosulfuron, clethodim, clodinafop(-propargyl), clomazone, clopyralid, clopyrasulfuron, cloransulam(-methyl), cumyluron, cyanazine, cycloate, cyclosulfamuron, cycloxydim, cyhalofop(-butyl), 2,4-D, 2,4-DB, 2,4-DP, desmedipham, diallate, dicamba, diclofop(-methyl), difenzoquat, diflufenican, dimefuron, dimepiperate, dimethachlor, dimethametryn, dimethenamid, dinitramine, diphenamid, diquat, dithiopyr, diuron, dymron, EPTC, esprocarb, ethalfluralin, ethametsulfuron(-methyl), ethofumesate, ethoxyfen, etobenzanid, fenoxaprop-ethyl, flamprop(-isopropyl), flamprop(-isopropyl-L), flamprop(-methyl), flazasulfuron, fluazifop(-butyl), flumetsulam, flumiclorac(-pentyl), flumioxazin, flumipropyn, fluometuron, fluorochloridone, fluoroglycofen(-ethyl), flupoxam, flupropacil, flurenol, fluridone, fluroxypyr, flurprimidol, flurtamone, fomesafen, glufosinate(-ammonium), glyphosate(-isopropylammonium), halosafen, haloxyfop(-ethoxyethyl), hexazinone, imazamethabenz(-methyl), imazamethapyr, imazamox, imazapyr, imazaquin, imazethapyr, imazosulfiron, ioxynil, isopropalin, isoproturon, isoxaben, isoxaflutole, isoxapyrifop, lactofen, lenacil, linuron, MCPA, MCPP, mefenacet, metamitron, metazachlor, methabenzthiazuron, metobenzuron, metobromuron, metolachlor, metosulam, metoxuron, metribuzin, metsulfuron-(-methyl), molinate, monolinuron, naproanilide, napropamide, neburon, nicosulfuron, norflurazon orbencarb, oryzalin, oxadiazon, oxyfluorfen, paraquat, pendimethalin, phenmedipham, piperophos, pretilachlor, primisulfuron(-methyl), prometryn, propachlor, propanil, propaquizafop, propyzamide, prosulfocarb, prosulfuron, pyrazolate, pyrazosulfuron(-ethyl), pyrazoxyfen, pyributicarb, pyridate, pyrithiobac(-sodium) quinchlorac, quinmerac, quizalofop(-ethyl), quizalofop(-p-tefuryl), rimsulfuron, sethoxydim, simazine, simetryn, sulcotrione, sulfentrazone, sulfometuron(-methyl), sulfosate, tebutam, tebuthiuron, terbuthylazine, terbutryn, thenylchlor, thiafluamide, thiazopyr, thidiazimin, thifensulfuron(-methyl), thiobencarb, tiocarbazil, tralkoxydim, triallate, triasulfuiron, tribenuron(-methyl), triclopyr, tridiphane, trifluralin and triflusulfuron.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 5 kg per ha.

The preparation and use of the active compounds according to the invention can be seen from the Examples below.

PREPARATION EXAMPLES

Example 1

(Process (a))

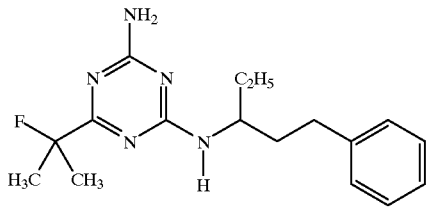

At approximately 22° C., a mixture of 2.0 g (7 mmol) of (R/S)-1-(1-ethyl-3-phenyl-propyl)-biguanide hydrochloride (racemic), 1.89g (14 mmol) of ethyl 2-fluoro-isobutyrate, 0.76 g (14 mmol) of sodium methoxide and 12 ml of methanol is stirred for about 15 hours. The mixture is then diluted to about 3 times its original volume using water and shaken with ethyl acetate, and the organic phase is separated off washed with water, dried with sodium sulphate and filtered. The solvent is carefully distilled off from the filtrate under water pump vacuum. The residue is purified by column chromatography (silica gel, ethyl acetate).

This gives 1.44 g (64% of theory) of (R/S)-2-amino-4-(1-fluoro-1-methyl-ethyl)-6-(1-ethyl-3-phenyl-propylamino)-1,3,5-triazine (racemate).

By the method of Example 1 and in accordance with the general description of preparation processes according to the invention, it is also possible to prepare, for example, the compounds of the formula (I) listed in Table 1 below.

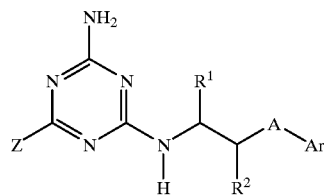

(I)

TABLE 1

Examples of compounds of the formula (I)

| Ex. No. | R¹ | R² | A | Ar | Z | Physical data and stereochemical specifications |
|---|---|---|---|---|---|---|
| 2 | $C_2H_5$ | H | O | ⟨phenyl⟩ | $CF_3$ | m.p.: 100° C. (racemate) |
| 3 | $C_2H_5$ | H | O | ⟨phenyl⟩ | $CF_3$ | (amorphous) (R enantiomer) |
| 4 | $C_2H_5$ | H | O | ⟨phenyl⟩ | $CF_3$ | (amorphous) (S enantiomer) |
| 5 | $C_2H_5$ | H | $CH_2$ | ⟨4-$OCH_3$-phenyl⟩ | $CF_3$ | (racemate) |
| 6 | $C_2H_5$ | H | $CH_2$ | ⟨4-$OCH_3$-phenyl⟩ | $CF_3$ | (R enantiomer) |
| 7 | $C_2H_5$ | H | $CH_2$ | ⟨4-$OCH_3$-phenyl⟩ | $CF_3$ | (S enantiomer) |
| 8 | $C_2H_5$ | H | $CH_2$ | ⟨4-$SCH_3$-phenyl⟩ | $CF(CH_3)_2$ | (amorphous) (racemate) |
| 9 | $C_2H_5$ | H | $CH_2$ | ⟨4-$SCH_3$-phenyl⟩ | $CF(CH_3)_2$ | (R enantiomer) |

TABLE 1-continued

Examples of compounds of the formula (I)

| Ex. No. | R¹ | R² | A | Ar | Z | Physical data and stereochemical specifications |
|---|---|---|---|---|---|---|
| 10 | $C_2H_5$ | H | $CH_2$ | 4-(SCH₃)-phenyl | $CF(CH_3)_2$ | (S enantiomer) |
| 11 | $C_2H_5$ | H | $CH_2$ | 2-thienyl | $CF_3$ | (amorphous) (racemate) |
| 12 | $C_2H_5$ | H | $CH_2$ | 3-thienyl | $CF_3$ | (amorphous) (racemate) |
| 13 | $C_2H_5$ | H | $CH_2$ | 2-chloropyridin-5-yl | $CF_3$ | m.p.: 74° C. (racemate) |
| 14 | $C_2H_5$ | H | $CH_2$ | pyridin-2-yl | $CF_3$ | (amorphous) (racemate) |
| 15 | $C_2H_5$ | H | $CH_2$ | pyridin-3-yl | $CF_3$ | (amorphous) (racemate) |
| 16 | $C_2H_5$ | H | $CH_2$ | pyridin-4-yl | $CF_3$ | (amorphous) (racemate) |
| 17 | $C_2H_5$ | H | O | 2-(C(CH₃)₃)-pyrimidin-5-yl | $CF_3$ | (amorphous) (racemate) |
| 18 | $C_2H_5$ | H | $CH_2$ | 2-chloropyridin-5-yl | $CHFCH_3$ | (amorphous) (racemate) |
| 19 | $C_2H_5$ | H | $CH_2$ | 3-thienyl | $CHFCH_3$ | (amorphous) (racemate) |
| 20 | $C_2H_5$ | H | $CH_2$ | pyridin-3-yl | $CHFCH_3$ | (amorphous) (racemate) |

TABLE 1-continued

Examples of compounds of the formula (I)

| Ex. No. | R¹ | R² | A | Ar | Z | Physical data and stereochemical specifications |
|---|---|---|---|---|---|---|
| 21 | $C_2H_5$ | H | $CH_2$ | 2-pyridyl | $CHFCH_3$ | (amorphous) (racemate) |
| 22 | $C_2H_5$ | H | $CH_2$ | 2-pyridyl | $CF(CH_3)_2$ | (amorphous) (racemate) |
| 23 | $C_2H_5$ | H | $CH_2$ | 2-thienyl | $CHFCH_3$ | (amorphous) (racemate) |
| 24 | $C_2H_5$ | H | $CH_2$ | 2-thienyl | $CF(CH_3)_2$ | (amorphous) (racemate) |
| 25 | $C_2H_5$ | H | $CH_2$ | 6-chloropyridin-3-yl | $CF(CH_3)_2$ | (amorphous) (racemate) |
| 26 | $C_2H_5$ | H | $CH_2$ | 3-pyridyl | $CF(CH_3)_2$ | (amorphous) (racemate) |
| 27 | $C_3H_7$-i | H | $CH_2$ | 4-chlorophenyl | $CF_3$ | (amorphous) (racemate) |
| 28 | $C_3H_7$-i | H | $CH_2$ | 4-chlorophenyl | $CHFCH_3$ | (amorphous) (racemate) |
| 29 | $C_3H_7$-i | H | $CH_2$ | 4-chlorophenyl | $CF(CH_3)_2$ | (amorphous) (racemate) |
| 30 | $C_3H_7$-n | H | $CH_2$ | 4-chlorophenyl | $CF(CH_3)_2$ | (amorphous) (racemate) |
| 31 | $C_3H_7$-n | H | $CH_2$ | 4-chlorophenyl | $CHFCH_3$ | (amorphous) (racemate) |
| 32 | $C_3H_7$-n | H | $CH_2$ | 4-chlorophenyl | $CF_3$ | (amorphous) (racemate) |

TABLE 1-continued

Examples of compounds of the formula (I)

| Ex. No. | R¹ | R² | A | Ar | Z | Physical data and stereochemical specifications |
|---|---|---|---|---|---|---|
| 33 | $C_2H_5$ | H | $CH_2$ | 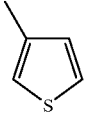 | $CF(CH_3)_2$ | (amorphous) (racemate) |
| 34 | $C_2H_5$ | H | $CH_2$ | 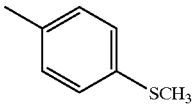 | $CF_3$ | (amorphous) (racemate) |
| 35 | $C_2H_5$ | H | $CH_2$ | 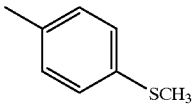 | $CHFCH_3$ | (amorphous) (racemate) |
| 36 | $C_2H_5$ | H | O | 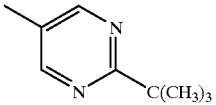 | $CHFCH_3$ | (amorphous) (racemate) |
| 37 | $C_2H_5$ | H | O | 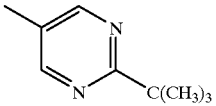 | $CF(CH_3)_2$ | (amorphous) (racemate) |
| 38 | $C_2H_5$ | H | O | 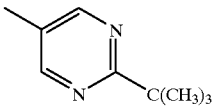 | $C_2H_5$ | (amorphous) (racemate) |
| 39 | $C_2H_5$ | H | O | 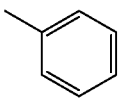 | $CHFCH_3$ | (amorphous) (racemate) |
| 40 | $C_2H_5$ | H | O | 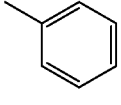 | $C_2H_5$ | (amorphous) (racemate) |
| 41 | $C_2H_5$ | H | $CH_2$ | 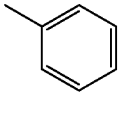 | $CF_3$ | (amorphous) (racemate) |
| 42 | $C_2H_5$ | H | O | 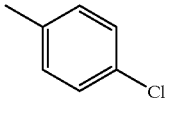 | $CF_3$ | (amorphous) (racemate) |
| 43 | $C_2H_5$ | H | $CH_2$ |  | $CF_3$ | (amorphous) (S enantiomer) |

TABLE 1-continued

Examples of compounds of the formula (I)

| Ex. No. | R¹ | R² | A | Ar | Z | Physical data and stereochemical specifications |
|---|---|---|---|---|---|---|
| 44 | $C_2H_5$ | H | O | 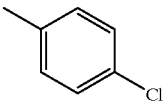 | $CF_3$ | (amorphous) (S enantiomer) |
| 45 | $C_2H_5$ | H | $CH_2$ | 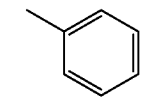 | $CF_3$ | (amorphous) (R enantiomer) |
| 46 | $C_2H_5$ | H | O | 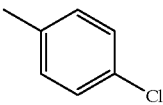 | $CF_3$ | (amorphous) (R enantiomer) |
| 47 | $C_2H_5$ | H | $CH_2$ | 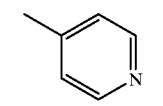 | $CF(CH_3)_2$ | (amorphous) (racemate) |
| 48 | $C_2H_5$ | H | $CH_2$ | 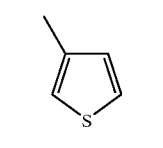 | $C_2H_5$ | (amorphous) (racemate) |
| 49 | $C_2H_5$ | H | $CH_2$ | 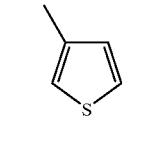 | $CH_2OCH_3$ | (amorphous) (racemate) |
| 50 | $C_2H_5$ | H | $CH_2$ | 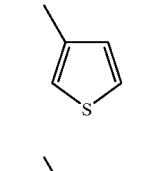 | $CH_2SCH_3$ | (amorphous) (racemate) |
| 51 | $C_2H_5$ | H | $CH_2$ | 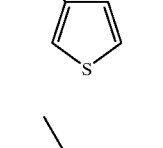 | $CHClCH_3$ | (amorphous) (racemate) |
| 52 | $C_2H_5$ | H | $CH_2$ | 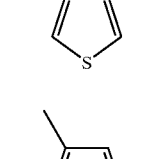 | $CHCl_2$ | (amorphous) (racemate) |
| 53 | $C_2H_5$ | H | $CH_2$ | 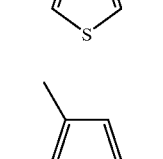 | $C_2H_4OCH_3$ | (amorphous) (racemate) |
| 54 | $C_2H_5$ | H | $CH_2$ | 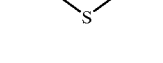 | $CH_2CH(OCH_3)_2$ | (amorphous) (racemate) |

TABLE 1-continued

Examples of compounds of the formula (I)

| Ex. No. | $R^1$ | $R^2$ | A | Ar | Z | Physical data and stereochemical specifications |
|---|---|---|---|---|---|---|
| 55 | $C_2H_5$ | H | $CH_2$ | 2-thienyl | $C_2H_4OCH_3$ | (amorphous) (racemate) |
| 56 | $C_2H_5$ | H | $CH_2$ | 2-thienyl | $CH_2CH(OCH_3)_2$ | (amorphous) (racemate) |
| 57 | $C_2H_5$ | H | $CH_2$ | 2-thienyl | $C_2H_5$ | (amorphous) (racemate) |
| 58 | $C_2H_5$ | H | $CH_2$ | 2-thienyl | $CH_2OCH_3$ | (amorphous) (racemate) |
| 59 | $C_2H_5$ | H | $CH_2$ | 2-thienyl | $CH_2SCH_3$ | (amorphous) (racemate) |
| 60 | $C_2H_5$ | H | $CH_2$ | 2-thienyl | $CHClCH_3$ | (amorphous) (racemate) |
| 61 | $C_2H_5$ | H | $CH_2$ | 2-thienyl | $CHCl_2$ | (amorphous) (racemate) |

Starting Materials of the Formula (II):

Example (II-1)

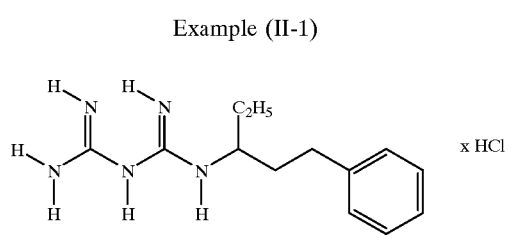

A mixture of 2.9 g (14.5 mmol) of 1-ethyl-3-phenyl-propylamine hydrochloride (racemic), 1.22 g (14.5 mmol) of cyanoguanidine (dicyandiamide) and 30 ml of 1,2-dichloro-benzene is heated at 140° C. to 150° C for 8 hours. The crystalline product which is obtained after cooling is isolated by filtration with suction.

This gives 3.6 g (87% of theory) of 1-(1-ethyl-3-phenyl-propyl)-biguanide hydrochloride (racemate).

The reaction can be carried out at the same temperature even without solvent—i.e. in the melt.

By the method of Example (II-1), it is also possible to prepare, for example, the compounds of the formula (II) and their hydrochlorides listed in Table 2 below.

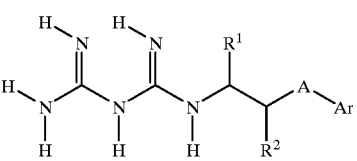 (II)

TABLE 2

Examples of compounds of the formula (II) - (hydrochlorides)

| Ex. No. | $R^1$ | $R^2$ | A | Ar | Physical data and stereochemical specifications |
|---|---|---|---|---|---|
| (II-2) | $C_2H_5$ | H | O | phenyl | (racemate) |

TABLE 2-continued

Examples of compounds of the formula (II) - (hydrochlorides)

| Ex. No. | R¹ | R² | A | Ar | Physical data and stereochemical specifications |
|---|---|---|---|---|---|
| (II-3) | $C_2H_5$ | H | $CH_2$ | 4-methoxyphenyl | (racemate) |
| (II-4) | $C_2H_5$ | H | $CH_2$ | 4-methylthiophenyl | (racemate) |
| (II-5) | $C_2H_5$ | H | $CH_2$ | 4-methylsulfinylphenyl ($SOCH_3$) | (racemate) |
| (II-6) | $C_2H_5$ | H | $CH_2$ | 4-methylsulfonylphenyl ($SO_2CH_3$) | (racemate) |
| (II-7) | $C_2H_5$ | H | $CH_2$ | 2-thienyl | (racemate) |
| (II-8) | $C_2H_5$ | H | $CH_2$ | 3-thienyl | (racemate) |
| (II-9) | $C_2H_5$ | H | $CH_2$ | 6-chloropyridin-3-yl | (racemate) |
| (II-10) | $C_2H_5$ | H | $CH_2$ | pyridin-2-yl | (racemate) |
| (II-11) | $C_2H_5$ | H | $CH_2$ | pyridin-3-yl | (racemate) |
| (II-12) | $C_2H_5$ | H | $CH_2$ | pyridin-4-yl | (racemate) |
| (II-13) | $C_2H_5$ | H | O | 2-tert-butylpyrimidin-5-yl | (amorphous) (hydrochloride) (racemate) |

Starting Materials of the Formula (V):

Example (V-1)

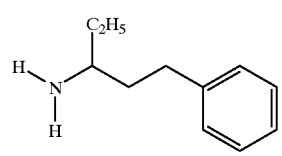

Step 1

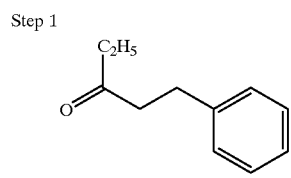

A mixture of 19.3 g (0.134 mol) of ethyl propionyl acetate, 7.5 g (0.11 mol) of sodium methoxide, 60 ml of ethanol and 50 ml of 10% strength aqueous sodium hydroxide solution is initially charged at room temperature (approximately 20° C.) and the reaction mixture is, after dropwise addition of 12.6 g (0.10 mol) of benzyl chloride, stirred at approximately 60° C. for about 5 hours. The mixture is subsequently concentrated under water pump vacuum and the residue is stirred with 50 ml of 10% strength sodium hydroxide solution at approximately 60° C. for 3 hours. The pH is then adjusted to 4 using 10% strength aqueous hydrochloric acid, and the mixture is shaken with diethyl ether. The organic phase is dried with sodium sulphate and filtered. The filtrate is concentrated under water pump vacuum and the residue is purified by column chromatography (silica gel/ethyl acetate).

This gives 13.9 g (85% of theory) of 1-phenyl-pentan-3-one.

Step 2

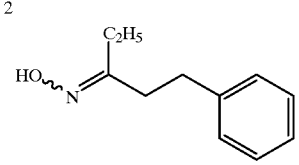

A mixture of 13.9 g (86 mmol) of 1-phenyl-pentan-3-one, 8.9 g (128 mmol) of hydroxylamine hydrochloride and 10.1 g (128 mmol) of pyridine is stirred at approximately 75° C. for 2 hours. After cooling, the mixture is shaken with water/ethyl acetate and the organic phase is separated off, dried with sodium sulphate and filtered. The solvent is carefully distilled off from the filtrate under water pump vacuum. The residue, which essentially contains the compound 1-phenyl-pentan-3-one oxime of the above formula, is employed for the next step without any further purification.

Step 3

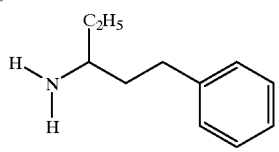

With stirring, 6.5 g (0.17 mol) of lithium aluminium hydride in 130 ml of tetrahydrofuran are added to a mixture of the product obtained in accordance with the description of step 2 and 130 ml of tetrahydrofuran, and the reaction mixture is stirred at approximately 60° C. for 30 minutes. After cooling, the mixture is admixed with a solution of 1 g of sodium hydroxide in 30 ml of water, and the mixture is stirred at approximately 60° C. for 30 minutes. After cooling, the mixture is filtered and the filtrate is concentrated under water pump vacuum. The residue is purified by column chromatography (silica gel, ethyl acetate).

This gives 6.3 g (45% of theory) of (R/S)-1-ethyl-3-phenyl-propylamine (racemate).

Use Examples

Example A

Pre-emergence-test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is watered with the preparation of active compound. The amount of water per unit area is advantageously kept constant. The concentration of active compound in the preparation is immaterial, only the application rate of active compound per unit area matters.

After three weeks, the degree of damage to the plants is scored visually in % damage in comparison to the development of the untreated control.

The figures denote:

0%=no effect (like untreated control)

100%=total destruction

In this test, the compounds of Preparation Examples 1, 2, 12, 19, 21, 22, 29, 33, 41 and 45, for example, show strong activity against weeds, and some of them are tolerated well by crop plants, such as, for example, maize, wheat and cotton (cf. Table A).

In the tables below, "ai" means "active ingredient".

TABLE A

| | Pre-emergence test/greenhouse | | | | | | |
|---|---|---|---|---|---|---|---|
| Active compound of Preparation Ex. No. | Application rate (g of ai./ha) | Wheat | Cotton | Cheno-podium | Solanium | Veronica | Viola |
| (22) | 500 | 0 | 0 | 100 | 100 | 100 | 100 |

| Active compound of Preparation Ex. No. | Application rate (g of ai./ha) | Maize | Cotton | Alope-curus | Digi-taria | Abu-tilon | Galium | Matri-caria |
|---|---|---|---|---|---|---|---|---|
| (1) | 500 | 0 | 0 | 100 | 100 | 100 | 100 | 100 |

Appli-

TABLE A-continued

Pre-emergence test/greenhouse

| Active compound of Preparation Ex. No. | cation rate (g of ai./ha) | Wheat | Digitaria | Echinochloa | Abutilon | amaranthus | Datura | Polygonum | Veronica |
|---|---|---|---|---|---|---|---|---|---|
| (12) | 500 | 0 | 80 | 100 | 100 | 100 | 100 | 100 | 100 |
| (19) | 500 | 0 | 100 | 100 | 100 | 100 | 100 | 100 | 100 |

| Active compound of Preparation Ex. No. | Application rate (g of ai./ha) | Maize | Abutilon | Amaranthus | Sinapis |
|---|---|---|---|---|---|
| (2) | 1000 | 20 | 80 | 100 | 100 |

| Active compound of Preparation Ex. No. | Application rate (g of ai./ha) | Alopecurus | Setaria | Abutilon | Amaranthus | Galium |
|---|---|---|---|---|---|---|
| (21) | 1000 | 100 | 90 | 90 | 95 | 80 |
|  | 1000 | 90 | 70 | 100 | 95 | 100 |

Example B

Post-emergence-test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of active compound such that the particular amounts of active compounds desired are applied per unit area. The concentration of the spray liquor is chosen so that the particular amounts of active compound desired are applied in 1000 l of water/ha.

After three weeks, the degree of damage to the plants is scored visually in % damage in comparison to the untreated control.

The figures denote:

0%=no effect (like untreated control)

100%=total destruction

In this test, the compounds of Preparation Examples 1, 2, 4, 11, 12, 19, 22, 23, 24, 33, 41, 43, 44, 45 and 46, for example, show strong activity against weeds, and some of them are tolerated well by crop plants, such as, for example, maize and wheat (cf. Table B).

TABLE B

Post-emergence test/greenhouse

| Active compound of Preparation Ex. No. | Application rate (g of ai./ha) | Wheat | Echinochloa | Abutilon | Datura | Ipomoea | Veronica |
|---|---|---|---|---|---|---|---|
| 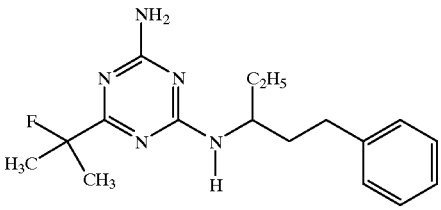 (1) | 250 | 0 | 80 | 100 | 100 | 100 | 100 |

| Active compound of Preparation Ex. No. | Application rate (g of ai./ha) | Maize | Setaria | Amaranthus | Xanthium |
|---|---|---|---|---|---|
| 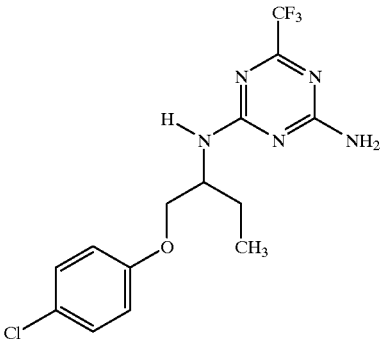 (46) | 1000 | 0 | 100 | 100 | 70 |

| Active compound of Preparation Ex. No. | Application rate (g of ai./ha) | Wheat | Echinochloa | Setaria | Amaranthus | Ipomoea | Polygonum | Solanum |
|---|---|---|---|---|---|---|---|---|

TABLE B-continued
Post-emergence test/greenhouse
| | | | | | | | | |
|---|---|---|---|---|---|---|---|---|
| 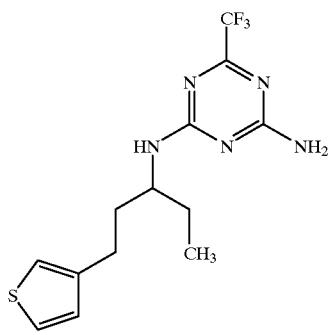 (12) | 500 | 10 | 90 | 95 | 100 | 100 | 100 | 100 |
| 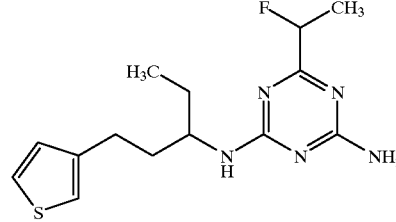 (19) | 500 | — | 100 | 100 | 100 | 100 | 100 | 100 |
| 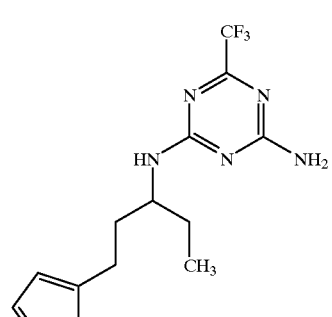 (11) | 500 | 10 | 80 | 95 | 100 | 100 | 100 | 100 |
| 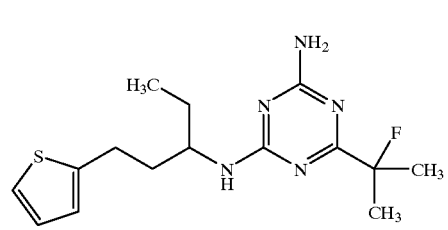 (24) | 500 | — | 100 | 80 | 100 | 100 | 95 | 95 |
| 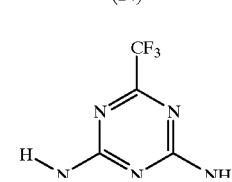 | 500 | 10 | — | 90 | 100 | 100 | 100 | 100 |

What is claimed is:

1. A substituted 2-amino-4-alkylamino-1,3,5-triazine represented by the following formula (I),

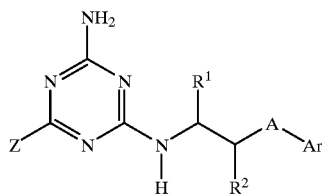

wherein
$R^1$ represents $C_2$–$C_4$ alkyl; $C_3$–$C_6$ cycloalkyl; hydroxyl-, cyano-, halogen- or $C_1$–$C_4$-alkoxy-substituted $C_2$–$C_4$ alkyl; or cyano-, halogen- or $C_1$–$C_4$-alkyl-substituted $C_3$–$C_6$ cycloalkyl, $R^2$ represents hydrogen or $C_1$–$C_4$ alkyl, A represents oxygen or methylene, Ar represents phenyl; naphthyl; heterocyclyl; substituted phenyl; substituted naphthyl; or substituted heterocyclyl;

wherein heterocyclyl is a member selected from the group consisting of furyl, benzofuryl, dihydrobenzofuryl, tetrahydrofuryl, thienyl, benzothienyl, thiazolyl, benzothiazolyl, oxazolyl, benzoxazolyl, thiadiazolyl, oxadiazolyl, pyrazolyl, pyrrolyl, quinolinyl, isoquinolinyl, pyridinyl and pyrimidinyl; and wherein the substituents of the substituted phenyl, substituted naphthyl, and substituted heterocyclyl are each selected independently from the group consisting of hydroxyl; cyano; nitro; halogen; $C_1$–$C_6$ alkyl; hydroxy-, cyano- or halogen-substituted $C_{1-C6}$ alkyl; $C_1$–$C_6$ alkoxy; hydroxy-, cyano- or halogen-substituted $C_1$–$C_6$ alkoxy; $C_{1-C6}$ alkylcarbonyl; $C_1$–$C_6$ alkoxycarbonyl; $C_1$–$C_6$ alkylthio; $C_1$–$C_6$ alkylsulphinyl; $C_{1-C6}$ alkylsulphonyl; halogen-substituted $C_{1-C6}$ alkylcarbonyl, $C_1$–$C_6$ alkoxycarbonyl, $C_{1-6}$ alkylthio, $C_{1-6}$ alkylsulphinyl, or $C_1$–$C_6$ alkylsulphonyl; phenyl; hydroxyl-, cyano-, nitro-, halogen-, $C_1$–$C_4$-alkyl, $C_1$–$C_4$-halogenoalkyl-, $C_{1-C4}$-alkoxy- or $C_{1-C4}$-halogenoalkoxy-substituted phenyl; phenoxy; hydroxyl-, cyano-, nitro-, halogen-, $C_{1-C4}$-alkyl, $C_{1-C4}$-halogenoalkyl-, $C_{1-C4}$-alkoxy- or $C_{1-C4}$-halogenoalkoxy-substituted phenoxy; methylenedioxy; halogen substituted methylenedioxy; ethylenedioxy; and halogen substituted ethylenedioxy, and Z represents hydrogen; $C_1$–$C_6$ alkyl; $C_1$–$C_6$ alkylcarbonyl; $C_{1-C6}$ alkoxycarbonyl; $C_1$–$C_6$ alkylsulphinyl; $C_1$–$C_6$ alkylsulphonyl; hydroxyl-, cyano-, nitro-, halogen-, $C_1$–$C_4$-alkoxy-, $C_1$–$C_4$-alkylcarbonyl-, $C_1$–$C_4$-alkoxycarbonyl-, $C_1$–$C_4$-alkylthio-, Cl -$C_4$-alkylsulphinyl- or $C_{1-C4}$-alkylsulphonyl-substituted $C_1$–$C_6$ alkyl, $C_1$–$C_6$ alkylcarbonyl, $C_1$–$C_6$ alkoxycarbonyl, $C_1$–$C_6$ alkylsulphinyl or $C_1$–$C_6$ alkylsulphonyl; alkenyl; halogen substituted alkenyl; alkynyl; or halogen substituted alkynyl, provided that when Ar represents phenyl or substituted phenyl, A does not represent methylene.

2. The substituted 2-amino-4-alkylamino-1,3,5-triazine of claim 1 wherein, $R^1$ represents ethyl, n- or i-propyl, n-, i-, s- or t-butyl; hydroxyl-, cyano-, fluorine-, chlorine-, methoxy- or ethoxy-substituted ethyl, n- or i-propyl, n-, i-, s- or t-butyl; cyclopropyl, cyclobutyl, cyclopentyl or cyclohexyl; or cyano-, fluorine-, chlorine-, methyl- or ethyl-substituted cyclopropyl, cyclobutyl, cyclopentyl or cyclohexyl, $R^2$ represents hydrogen, methyl or ethyl, for Ar the substituents of the substituted phenyl, substituted naphthyl and substituted heterocyclyl are each selected independently from the group consisting of hydroxy; cyano; nitro; fluorine; chlorine; bromine; methyl, ethyl, n- or i-propyl, n-, i-, s- or t-butyl, methoxy, ethoxy, n- or i-propoxy, n-, i-, s- or t-butoxy; hydroxyl-cyano-, fluorine- or chlorine-substituted methyl, ethyl, n- or i-propyl, n-, i-, s- or t-butyl, methoxy, ethoxy, n- or i-propoxy, n-, i-, s- or t-butoxy; acetyl, propionyl, n- or i-butyroyl, methoxycarbonyl, ethoxycarbonyl, n- or i-propoxycarbonyl, methylthio, ethylthio, n- or i-propylthio, methylsulphinyl, ethylsulphinyl, n- or i-propylsulphinyl, methylsulphonyl, ethylsulphonyl, n- or i-propylsulphonyl; fluorine- or chlorine-substituted acetyl, propionyl, n- or i-butyroyl, methoxycarbonyl, ethoxycarbonyl, n- or i-propoxycarbonyl, methylthio, ethylthio, n- or i-propylthio, methylsulphinyl, ethylsulphinyl, n- or i-propylsulphinyl, methylsulphonyl, ethylsulphonyl, n- or i-propylsulphonyl; phenyl; hydroxyl-, cyano-, nitro-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substituted phenyl; phenoxy; hydroxyl-, cyano-, nitro-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substituted phenoxy; methylenedioxy; fluorine- or chlorine-substituted methylenedioxy; ethylenedioxy; and fluorine- or chlorine-substituted ethylenedioxy, and Z represents hydrogen; methyl, ethyl, n- or i-propyl, n-, i-, s- or t-butyl, methylsulphinyl, ethylsulphinyl, n- or i-propylsulphinyl, methylsulphonyl, ethylsulphonyl, n- or i-propylsulphonyl; hydroxyl-, cyano-, nitro-, fluorine-, chlorine-, methoxy-, ethoxy-, n- or i-propoxy-, n-, i-, s- or t-butoxy-, methylthio-ethylthio-, n- or i-propylthio-, methylsulphinyl-, ethylsulphinyl-, n- or i-propylsulphinyl-, methylsulphonyl-, ethylsulphonyl-, n- or i-propylsulphonyl-substituted methyl, ethyl, n- or i-propyl, n-, i-, s- or t-butyl, methylsulphinyl, ethylsulphinyl, n- or i-propylsulphinyl, methylsulphonyl, ethylsulphonyl, n- or i-propylsulphonyl; ethenyl, propenyl, butenyl, ethynyl, propynyl or butynyl; or fluorine-, chlorine- or bromine-substituted ethenyl, propenyl, butenyl, ethynyl, propynyl or butynyl.

3. Method for controlling weeds, comprising the step of applying a herbicidally effective amount of compounds of the formula (I) according to claim 1 on weeds or their habitat.

4. A herbicidal composition comprising one or more compounds according to claim 1 and a member selected from the group consisting of an extender, a surfactant and mixtures thereof.

* * * * *